(12) United States Patent
McCanless et al.

(10) Patent No.: US 12,390,562 B2
(45) Date of Patent: Aug. 19, 2025

(54) ANTIMICROBIAL AND MICROSTATIC SENSOR SYSTEMS

(71) Applicant: ABBOTT DIABETES CARE INC., Alameda, CA (US)

(72) Inventors: Jonathan D. McCanless, Oakland, CA (US); Benjamin J. Feldman, Berkeley, CA (US)

(73) Assignee: ABBOTT DIABETES CARE INC., Alameda, CA (US)

(*) Notice: Subject to any disclaimer, the term of this patent is extended or adjusted under 35 U.S.C. 154(b) by 859 days.

(21) Appl. No.: 17/179,660

(22) Filed: Feb. 19, 2021

(65) Prior Publication Data

US 2021/0260257 A1 Aug. 26, 2021

Related U.S. Application Data

(60) Provisional application No. 62/979,169, filed on Feb. 20, 2020.

(51) Int. Cl.
*A61B 5/145* (2006.01)
*A61B 5/00* (2006.01)
(Continued)

(52) U.S. Cl.
CPC .......... *A61L 31/16* (2013.01); *A61B 5/14503* (2013.01); *A61B 5/6849* (2013.01); *A61L 31/088* (2013.01); *A61B 5/14532* (2013.01); *A61B 2560/0443* (2013.01); *A61L 2300/404* (2013.01); *A61L 2420/02* (2013.01); *A61L 2420/06* (2013.01)

(58) Field of Classification Search
None
See application file for complete search history.

(56) References Cited

U.S. PATENT DOCUMENTS 5,681,575 A 10/1997 Burrell et al.
7,179,849 B2 2/2007 Terry
(Continued)

FOREIGN PATENT DOCUMENTS

JP 2011-244804 A 12/2011
WO WO 2019/222615 A1 11/2019
(Continued)

OTHER PUBLICATIONS

WO, PCT/US21/18683 ISR and Written Opinion, Jun. 25, 2021.
(Continued)

*Primary Examiner* — Aurelie H Tu
(74) *Attorney, Agent, or Firm* — ONE LLP

(57) ABSTRACT

A sensor control device and methods of making them are described. The sensor control device includes an electronics housing and a plug assembly. The electronics housing includes an upper shell matable to a lower mount having a skin-facing surface. The plug assembly is coupled to the electronics housing and includes a sensor module that has a sensor and a sharp module having a sharp. The plug assembly includes a base having a skin-facing surface and a plug portion comprising a lumen therethrough. At least a portion of a surface of the electronics housing or the plug assembly comprises an antimicrobial agent. The antimicrobial agent may be a metal and/or a metal oxide.

15 Claims, 19 Drawing Sheets

(51) Int. Cl.
  *A61L 31/08*  (2006.01)
  *A61L 31/16*  (2006.01)

(56) References Cited

U.S. PATENT DOCUMENTS

| | | |
|---|---|---|
| 2005/0048124 A1 | 3/2005 | Sarangapani |
| 2006/0141015 A1 | 6/2006 | Tessier et al. |
| 2007/0135699 A1 | 6/2007 | Ward et al. |
| 2008/0161656 A1 | 7/2008 | Bruce et al. |
| 2010/0285084 A1* | 11/2010 | Yang ................ A61L 27/54 |
| | | 424/94.4 |
| 2013/0150691 A1 | 6/2013 | Pace et al. |
| 2014/0318949 A1 | 10/2014 | Wang et al. |
| 2016/0058380 A1 | 3/2016 | Lee et al. |
| 2016/0331283 A1 | 11/2016 | Rao et al. |
| 2018/0105927 A1 | 4/2018 | Mak et al. |
| 2019/0083017 A1 | 3/2019 | Walter |

FOREIGN PATENT DOCUMENTS

| | | |
|---|---|---|
| WO | WO 2019/236850 A1 | 12/2019 |
| WO | WO 2019/236859 A1 | 12/2019 |
| WO | WO 2019/236876 A1 | 12/2019 |

OTHER PUBLICATIONS

CA, 3,166,242 Examiner's Report, May 27, 2024.
EP, 21756503.5 Extended Search Report, Jan. 31, 2024.
CN, 202180012004.X First Office Action, Mar. 3, 2025.
JP, 2022-541635 Office Action, Dec. 11, 2024.

* cited by examiner

Ti - Cu - Ag

Ti - Ag - Cu

ANTIMICROBIAL AND MICROSTATIC SENSOR SYSTEMS

CROSS-REFERENCE TO RELATED APPLICATIONS

This application claims priority to, and the benefit of, U.S. Provisional Application No. 62/979,169, filed Feb. 20, 2020, which is hereby expressly incorporated by reference in its entirety for all purposes.

STATEMENT REGARDING FEDERALLY SPONSORED RESEARCH OR DEVELOPMENT

Not applicable.

BACKGROUND

The detection of various analytes within an individual can sometimes be vital for monitoring the condition of their health and well-being. Deviation from normal analyte levels can often be indicative of an underlying physiological condition, such as a metabolic condition or illness, or exposure to particular environmental factors or stimuli. Glucose levels, for example, can be particularly important to detect and monitor in diabetic individuals.

Analyte monitoring in an individual may take place periodically or continuously over a period of time. Periodic analyte monitoring may take place by withdrawing a sample of bodily fluid, such as blood, at set time intervals and analyzing ex vivo. Continuous analyte monitoring may be conducted using one or more sensors that remain implanted within a tissue of an individual, such as dermally, subcutaneously, or intravenously, through which analyses may take place in vivo. Implanted sensors may collect analyte data continuously, at planned intervals, or sporadically, depending on an individual's particular health needs and/or previously determined analyte levels.

Although the entirety of a sensor or sensing system may be implanted within an individual (e.g., surgically), it is more common for primarily the bioactive and communication path (e.g., flex circuit) portions of the sensor to be implanted internally (e.g., through a skin penetration), with one or more additional sensor components remaining external to the individual's body. In many instances, sensors suitable for measuring analyte levels in vivo may extend from a sensor housing that is designed to be worn "on-body" for extended periods of time, such as upon the skin. Such on-body analyte sensors may be especially desirable, because they often may be applied directly by a wearer, rather than relying on a medical professional to perform an invasive sensor implantation procedure.

Despite the desirability of on-body analyte sensors, their use may not be without complications. When positioning an on-body analyte sensor onto the skin of a wearer, a needle or other introducer is used to puncture the skin and allow implantation of at least a portion of a sensor through the dermal region. Accordingly, a transdermal skin wound is created in order for the sensor to undergo positioning for analyte monitoring (i.e., the "insertion site," including the actual wound and areas adjacent thereto), and at least an active portion of the sensor remains within the skin for the wear duration of the on-body analyte sensor. Both during localization and during wear, microorganism incursion into the wound at the sensor insertion site and along any length of the sensor, including the active area, may occur, such as by exposure to skin microorganisms and/or the external environment. The possibility of existing microorganisms near the insertion site and/or migration of microorganisms from adjacent areas, including the external environment, may create a rich environment for microorganism growth. Such growth may be harmful to the wearer and/or may lead to altered functioning of the analyte sensor itself, such as causing a shortened life of the sensor and/or providing erroneous or altered data or perceived sensitivity and/or response times.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
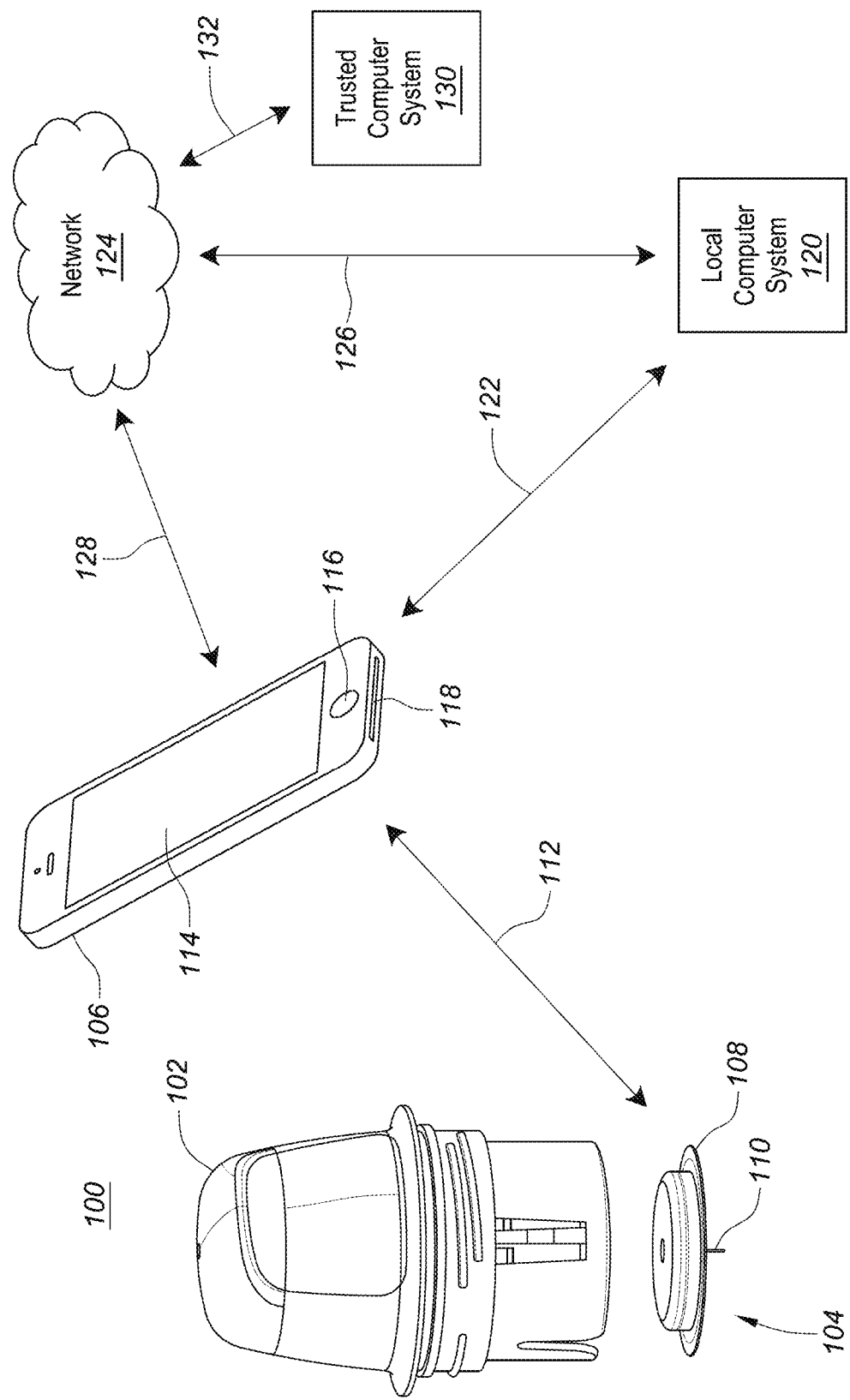
FIG. 1 is a conceptual diagram depicting an example analyte monitoring system that may incorporate one or more embodiments of the present disclosure.

The present disclosure generally describes on-body analyte sensor systems or sensor control devices that include an antimicrobial agent incorporated into at least a portion of a surface exposed to the environment. The sensor control devices include an electronics housing and a plug assembly. The electronics housing includes an upper shell matable to a lower mount having a skin-facing surface. The plug assembly is coupled to the electronics housing and includes a sensor module that has a sensor and a sharp module comprising a sharp. The plug assembly also includes a base having a skin-facing surface and a frustoconical, round, oval, or other shaped plug portion comprising a channel or lumen therethrough. At least a portion of a surface of the electronics housing or the plug assembly includes an antimicrobial agent, e.g., in a coating, or impregnated or mixed into the bulk material making up the electronics housing and/or plug assembly.

In some instances, on-body analyte sensors may provide a number of advantages when assaying physiological levels of various analytes, such as glucose, β-hydroxybutyrate, uric acid, ketone, creatinine, ethanol, and lactate. Continuous analyte monitoring using an implanted sensor can be advantageous, but there may be certain challenges associated with these types of measurements. Intravenous analyte sensors are invasive and can sometimes be painful for an individual to wear, particularly over an extended period. Subcutaneous, interstitial, or dermal analyte sensors can often be less painful for an individual to wear and can provide sufficient measurement accuracy in many cases.

Non-intravenous in vivo glucose-responsive analyte sensors have been developed over the past two decades by several manufacturers, and some have recently gained regulatory approval for monitoring glucose levels in diabetic individuals. Such glucose-responsive analyte sensors employ glucose oxidase that is covalently bound to a polymer to facilitate glucose detection and a transition metal complex (electron transfer agent or electron transfer mediator) to aid in conveyance of electrons released during the oxidation of glucose. In such sensors, the glucose-responsive analyte sensors respond rapidly to a change in glucose levels and provide a stable sensor response over a wear period of up to 10-14 days or longer. In vivo glucose-responsive analyte sensors available from other manufacturers also employ glucose oxidase and other glucose-related enzymes (e.g., flavin adenine dinucleotide-dependent glucose dehydrogenase (FAD-GDH)) as the basis for sensing but vary the sensing chemistry/protocol in various ways.

In vivo analyte sensors for assaying glucose and other analytes may include a membrane disposed over at least a portion of the implanted portion of the analyte sensor. In one aspect, the membrane may improve biocompatibility of the analyte sensor. In another aspect, the membrane may be permeable or semi-permeable to an analyte of interest and limit the overall analyte flux to the active area of the analyte sensor (i.e., sensing element(s)), such that the membrane functions as a mass transport limiting membrane. Limiting analyte access to the sensing element(s) of the analyte sensor with a mass transport limiting membrane can aid in avoiding sensor overload (saturation), thereby improving detection performance and accuracy. Such membranes may be highly specific toward limiting mass transport of a particular analyte, with other substances permeating through the membrane at significantly different rates, reducing background and interference signals from non-specific redox reactions with analyte molecules other than those of interests.

The wear duration of an on-body analyte sensor over an extended period of time (e.g., greater than two weeks, or even longer) may be limited in some instances. For example, analyte sensor chemistry can support long wear times, but there is also a desire to minimize the risk of infection or biofilm formation at or near the insertion site and the active area of the analyte sensor. Microorganism incursion into or near the operational components of an analyte sensor, such as the membrane or any other active area thereof (i.e., the sensing element(s)), may result in decreased accuracy and/or other loss of functionality, particularly during extended wear over multiple days or even longer over multiple weeks if microorganism incursion has occurred. In vivo on-body analyte sensors comprise a sensor tail component that may be implanted into a tissue of a user (e.g., transdermally, dermally, subcutaneously, or intravenously) and in some instances, as previously herein, the sensor tail includes one or more sensing elements at at least the distal tip thereof. As used herein, the term "sensor tail," and grammatical variants thereof, refers to the portion of the analyte sensor extending from the base of an external component thereof and of which at least a lower portion is inserted into the tissue of a wearer; the sensor tail of the present disclosure typically comprises one or more sensing elements at at least a lower portion thereof (e.g., at or near the distal tip), as described in greater detail herein below. In other embodiments, however, the distal tip of the sensor tail may not comprise the sensing elements, which may be located at a different (e.g., less distal) portion along the sensor tail. Regardless of the implantation qualities of the sensor as a whole (e.g., whether it be wholly or partially implanted into a tissue of a user), at least a portion of the sensor tail and active area thereof is in contact with bodily fluid once introduced to a tissue of a wearer.

Performance of on-body analyte sensors may be highly dependent upon biologic events local to or near the sensor tail. Typically, for accurate analyte measurement, an analyte sensor permits an undisturbed (i.e., consistent or predictable) pathway to communicate with the sensing element(s); likewise, the sensing element(s) (and potentially other elements, such as reference materials) must maintain communication with the intended body fluid of interest in an undisturbed or predictable manner. Moreover, for electrochemical sensors, stable connectivity (e.g., electrode connectivity and other electronics) is necessary to ensure proper analyte sensor functionality. Accordingly, maintaining such pathways and connectivity during the life of an on-body analyte sensor may be critical, including preventing microorganism incursion thereto.

Microorganisms may disturb the functionality of an on-body analyte sensor in one or more ways. For example, the disturbance may be a chemical disturbance and/or a physical disturbance. Accordingly, the antimicrobial (including microstatic) agents described herein for use in preventing or reducing microorganism interference with the functionality of an analyte sensor may be designed to combat any one or all types of potential microorganism disturbances.

For chemical disturbances, microorganisms may populate the insertion or implant site, i.e., the space adjacent to the implanted surface of the sensor, and influence analyte concentration located adjacent to the sensing element(s), thereby resulting in false analyte measurement readings. For example, such microorganisms may artificially increase or decrease the analyte level being measured by the sensing element(s). In certain instances, a microorganism layer (e.g., a dense microorganism layer or biofilm) may consume a portion of the one or more analytes being measured, such as glucose, before it contacts the sensing element(s) thereof, resulting in an artificially low analyte measurement. In other instances, an on-body analyte sensor may measure a host cell analyte and such analyte (e.g., lactate) may be erroneously measured due to microorganism infection at or near the insertion site, in which the microorganism generates the same analyte as metabolite or other secreted substance (e.g., cytokines, enzymes, etc.). In such instances, the measurement may be artificially high due to an additive effect between the host metabolite level and that of the microorganism. In yet another scenario, microorganisms can interfere with analyte sensor measurement by causing an immune response at or near the insertion site. For example, the measured analyte may be a host cell metabolite and an accumulation of such host cells in response to the infection may result in an artificially high analyte measurement. Microorganisms at the sensor implant site can also produce a localized environment that may affect sensor function. For example, because microorganisms and eukaryotic cells produce acidic metabolites, an analyte sensor that is pH-sensitive may produce artificially low or high analyte measurements due to microorganism infection or resultant user immune response. That is, the presence of the microorganism or immune response to such may result in increased cell densities and heightened metabolic activity by producing acid, which may reduce pH and lead to false analyte measurements.

For physical disturbances, microorganism incursion, such as infection at the insertion site or along the sensor tail, may result in formation of a biofilm. Biofilms are typically dense networks of microorganism cells (e.g., bacteria cells) embedded in DNA, proteins, polysaccharides, or other compounds and may result in erroneous analyte measurements by an analyte sensor. For example, the biofilm may interfere with diffusion of one or more analytes of interest to the sensing element(s) of the analyte sensor. In other scenarios, biofouling from protein or other molecule adsorption onto a surface of an analyte sensor, particularly the sensing element(s) thereof, may also interfere with diffusion of one or more analytes of interest, thereby resulting in artificially low analyte measurements. In certain situations, the membrane of a sensor may become desiccated or otherwise dried due to wound healing (e.g., healing at the insertion site of an on-body analyte sensor), effectively walling off the sensing element(s) and influencing the functionality of the analyte sensor. Moreover, such membrane desiccation may block the pathway to the sensing element(s) of the analyte sensor. In some instances, the various electrodes (e.g., working, reference, and/or counter electrodes) may lose connectivity due directly to the microorganism incursion (e.g., due to the desiccation of the membrane or biofilm formation) or indirectly from native immune cell recruitment in response to microorganism incursion.

The embodiments of the present disclosure accordingly impart an antimicrobial quality of one or more portions of an on-body analyte sensor in order to reduce or prevent malfunction due to microorganism incursion by incorporating antimicrobial compounds therewith. As used herein, the terms "antimicrobial" or "antimicrobial agent" or "antimicrobial compound," and grammatical variants thereof, refer to a substance or material that is detrimental (i.e., microbicidal) or microstatic (i.e., preventing or reducing colonization, expansion, and/or proliferation without necessarily being detrimental) to a microorganism, including bacteria, fungi, viruses, protozoans, and the like. The term "antimicrobial quality," used interchangeably herein with term "antimicrobial characteristic," and grammatical variants thereof, refers to any one or more components of the analyte sensors described herein having the ability to be detrimental or microstatic to a microorganism, and includes any mechanism, structure, system, or other technique for imparting said ability to a tangible material, including one or more components of the analyte sensors described herein.

Bacterial colonization of transcutaneous devices and sites are generally thought to derive from an external origin, such as that residing on the skin when infection manifests with extended implantation times or from contamination at the time of placement. The embodiments of the present disclosure reduce the risk of device contamination during placement and allows for protection from skin flora with regards to transcutaneous sensors. Implanted sensors would benefit from the inhibition of bacterial expansion within the implant site derived during and post-implantation.

In particular, the embodiments of the present disclosure utilize extracorporeal parts, such as the mount, shell, and/or plug of the sensor as a delivery system of antimicrobial and microstatic substances as a means of reducing or inhibiting the chemical and physical disturbances from microorganisms noted above. Antimicrobial substances may be blended into the bulk material and incorporated throughout (or layered via overmolding), applied as a thin layer to the surface(s) such as through sputter coating), or through a variety of impregnation methods that introduce the active agent in the outer region of the part.

The surfaces containing the antimicrobial agent may include, but are not limited to, at least one of the upper shell of the electronics housing, and in particular an upper facing surface of the upper shell, the skin-facing surface of the lower mount, the skin-facing surface of the base of the plug, an outward facing surface of the frustoconical portion of the plug, an upward facing surface of the frustoconical portion of the plug, and an exterior surface of the frustoconical portion of the plug.

The antimicrobial agent may be contained in a coating applied to the surface(s) of the sensor control device, may be blended into a bulk material used to make the inactive components of the sensor control device, may be incorporated throughout a material used to make the inactive components of the sensor control device, may be impregnated into the at least the portion of the surface of the inactive components of the sensor control device, may be applied onto the surface of the inactive components of the sensor control device via overmolding, and/or may be applied onto the surface of the inactive components of the sensor control device via sputter coating to form a layer containing an antimicrobial agent.

The antimicrobial agent may be a metal, such as silver, copper, zinc, and combinations thereof, and/or oxides thereof. For example, the antimicrobial agent may include silver and copper, e.g., silver on copper and copper on silver, and/or oxides thereof.

The antimicrobial agent may also be a metal oxide wherein the coating or surface contains at least 2% oxide, alternatively at least 5% oxide, alternatively at least 7% oxide, alternatively at least 10% oxide, alternatively at least 15% oxide, alternatively at least 25% oxide, alternatively at least 50% oxide, alternatively at least 75% oxide by weight. A highly oxidized metal oxide layer may be made by sputter coating a surface of the sensor control device with at least 5% oxidant, alternatively at least 10% oxidant, alternatively at least 15% oxidant, alternatively at least 20% oxidant, alternatively at least 25% oxidant, alternatively at least 30% oxidant, alternatively between about 5% to about 100%, alternatively between about 10% to about 95%, alternatively between about 40% to about 85%, alternatively between about 50% to about 85%, alternatively between about 60% and about 85%. The oxidant may be, for example, air or oxygen.

Before describing the analyte sensor systems of the present disclosure in further detail, a brief overview of suitable in vivo analyte sensor configurations and sensor systems employing the analyte sensors will be provided first so that the embodiments of the present disclosure may be better understood.

FIG. 1 is a conceptual diagram depicting an example analyte monitoring system 100 that may incorporate one or more embodiments of the present disclosure. The analyte monitoring system 100 (hereafter "the system 100") may be the same as or otherwise similar in some respects to the analyte monitoring system described and depicted in U.S. Patent Publ. No. 2016/0331283 entitled "Systems, Devices, and Methods for Assembling an Applicator and Sensor Control Device," the contents of which are hereby incorporated by reference in its entirety for all purposes.

A variety of analytes can be detected and quantified using the system 100 including, but not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, and troponin. The concentration of drugs, such as, but not limited to, antibiotics (e.g., gentamicin, vancomycin, and the like), digitoxin, digoxin, drugs of abuse, theophylline, and warfarin, may also be determined.

As illustrated, the system 100 includes a sensor applicator 102 (alternately referred to as an "inserter"), a sensor control device 104 (also referred to as an "in vivo analyte sensor control device"), and a reader device 106. The sensor applicator 102 is used to deliver the sensor control device 104 to a target monitoring location on a user's skin. Once delivered, the sensor control device 104 is maintained in position on the skin with an adhesive patch 108 coupled to the bottom of the sensor control device 104. A portion of a sensor 110 extends from the sensor control device 104 and is positioned such that it can be transcutaneously positioned and otherwise retained under the user's skin surface during the monitoring time period. While the sensor applicator and sensors are presented as two separate pieces in the figures, they can also be an integrated unit with a pre-assembled sterile sensor and electronics located in the applicator.

When the sensor control device 104 is properly assembled, the sensor 110 is placed in communication (e.g., electrical, mechanical, etc.) with one or more electrical components or sensor electronics included in the sensor control device 104. More specifically, the sensor control device 104 may include a printed circuit board having an application specific integrated circuit (ASIC) mounted thereto, and the sensor 110 may be operatively coupled to the ASIC which, in turn, may be coupled with an antenna and a power source. The sensor control device 104 is configured to communicate with the reader device 106 via a first communication path 112 using any wired or wireless technique. Suitable wireless protocols include, but are not limited to, radio frequency (RF) transmission, Wi-Fi, Bluetooth®, ZigBee®, near field communication (NFC), infrared, or any combination thereof.

A user can monitor applications installed in memory on the reader device 106 using a screen 114 and an input 116, and the reader device 106 can be recharged using a power port 118. The applications can include data communicated from the sensor 110 and/or display information provided by the sensor 110. The reader device 106 may comprise, but is not limited to, a dedicated handheld device, a smartphone, or other computing device. The reader device 106 may communicate with a local computer system 120 via a second communication path 122 using any wired or wireless technique. The local computer system 120 may comprise, but is not limited to, a laptop, a desktop, a tablet, a phablet (combination phone/tablet), a smartphone, a set-top box, a video game console, or other computing device. Suitable wireless protocols for communicating across the communication path 122 are similar to those of the first communication path 112.

The local computer system 120 can communicate with a network 124 via a third communication path 126, and the reader device 106 can communicate with the network 124 via a fourth communication path 128. The third and fourth communication paths 126, 128 can comprise any of the wired or wireless technique mentioned herein. The network 124 can be any of a number of networks, such as a private network, a public network, a local area or wide area network, and so forth. A trusted computer system 130 can communicate with the network 124 via a fifth communications path 132 by any wired or wireless technique mentioned herein. The trusted computer system 130 may include a server and can provide authentication services and secured data storage.

In the illustrated embodiment, the system 100 may comprise what is known as a "two-piece" architecture that requires final assembly by a user before the sensor 110 can be properly delivered to the target monitoring location. More specifically, the sensor 110 and the associated electrical components included in the sensor control device 104 are provided to the user in multiple (two) packages, where each may or may not be sealed with a sterile barrier but are at least enclosed in packaging. The user must open the packaging and follow instructions to manually assemble the components and subsequently deliver the sensor 110 to the target monitoring location with the sensor applicator 102.

Figure 2A:
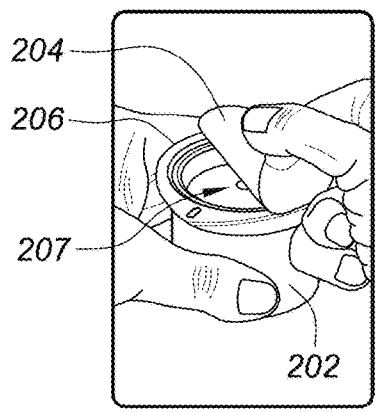
FIGS. 2A-2G are progressive views of the assembly and application of the system of FIG. 1 incorporating a two-piece architecture.
Figure 2B:
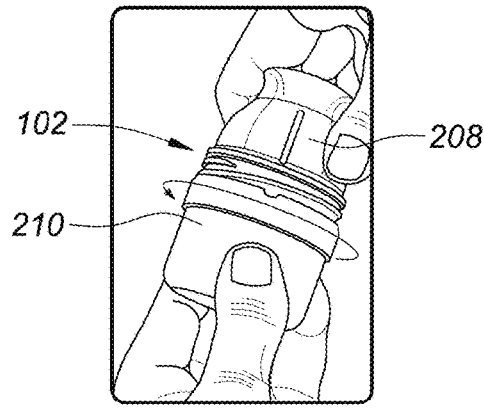

FIGS. 2A-2G are progressive views of the assembly and application of the system 100 incorporating a two-piece architecture. Additional assemblies are described in International Application Nos. PCT/US2019/035797 (published as WO 2019/236850), PCT/US2019/035810 (published as WO 2019/236859), and PCT/US2019/035829 (published as WO 2019/236876), all of which are hereby expressly incorporated by reference in their entirety for all purposes. FIGS. 2A and 2B depict the first and second packages, respectively, provided to the user for final assembly. More specifically, FIG. 2A depicts a sensor container or tray 202 that has a removable lid 204. The user prepares the sensor tray 202 by removing the lid 204, which acts as a sterile barrier to protect the internal contents of the sensor tray 202 and otherwise maintain a sterile internal environment. Removing the lid 204 exposes a platform 206 positioned within the sensor tray 202, and a plug assembly 207 (partially visible) is arranged within and otherwise strategically embedded within the platform 206. The plug assembly 207 includes a sensor module (not shown) and a sharp module (not shown). The sensor module carries the sensor 110 (FIG. 1), and the sharp module carries an associated sharp used to help deliver the sensor 110 transcutaneously under the user's skin during application of the sensor control device 104 (FIG. 1).

FIG. 2B depicts the sensor applicator 102 and the user preparing the sensor applicator 102 for final assembly. The sensor applicator 102 includes a housing 208 sealed at one end with a cap 210. The cap 210 provides a barrier that protects the internal contents of the sensor applicator 102. In particular, the sensor applicator 102 contains an electronics housing (not shown) that retains the electrical components for the sensor control device 104 (FIG. 1), and the cap 210 may or may not maintain a sterile environment for the electrical components. Preparation of the sensor applicator 102 includes uncoupling the housing 208 from the cap 210, which can be accomplished by unscrewing the cap 210 from the housing 208. The cap 210 can then be discarded or otherwise placed aside.

Figure 2C:
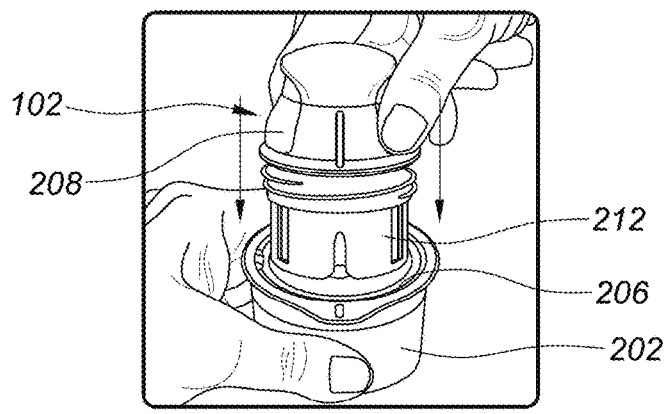

FIG. 2C depicts the user inserting the sensor applicator 102 into the sensor tray 202. The sensor applicator 102 includes a sheath 212 configured to be received by the platform 206 to temporarily unlock the sheath 212 relative to the housing 208, and also temporarily unlock the platform 206 relative to the sensor tray 202. Advancing the housing 208 into the sensor tray 202 results in the plug assembly 207 (FIG. 2A) arranged within the sensor tray 202, including the sensor and sharp modules, being coupled to the electronics housing arranged within the sensor applicator 102.

Figure 2D:
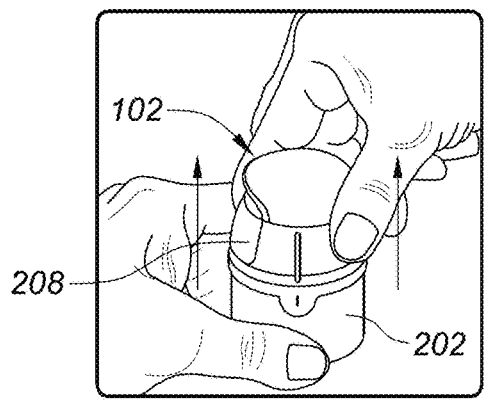

In FIG. 2D, the user removes the sensor applicator 102 from the sensor tray 202 by proximally retracting the housing 208 with respect to the sensor tray 202.

Figure 2E:
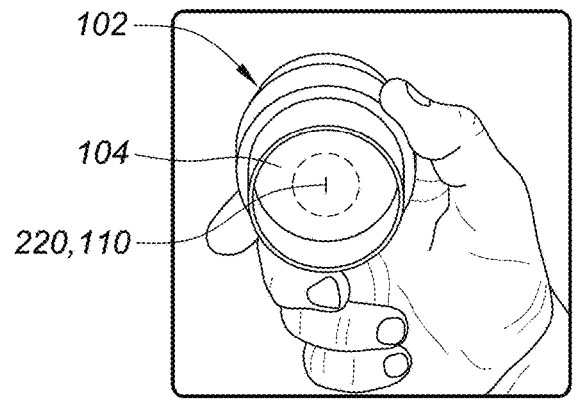

FIG. 2E depicts the bottom or interior of the sensor applicator 102 following removal from the sensor tray 202 (FIG. 2). The sensor applicator 102 is removed from the sensor tray 202 with the sensor control device 104 fully assembled therein and positioned for delivery to the target monitoring location. As illustrated, a sharp 220 extends from the bottom of the sensor control device 104 and carries a portion of the sensor 110 within a hollow or recessed portion thereof. The sharp 220 is configured to penetrate the skin of a user and thereby place the sensor 110 into contact with bodily fluid.

Figure 2F:
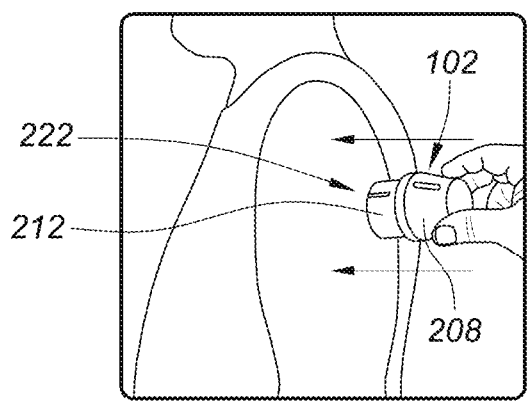
Figure 2G:
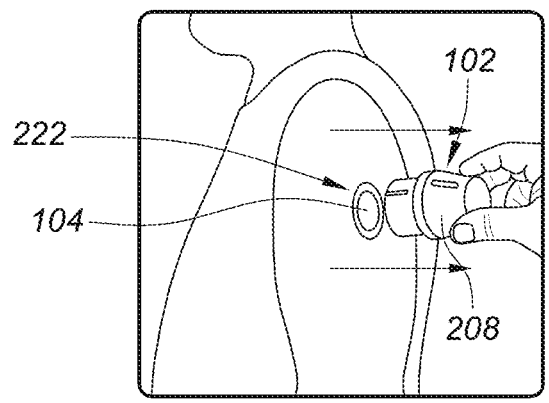

FIGS. 2F and 2G depict example delivery of the sensor control device 104 to a target monitoring location 222, such as the back of an arm of the user. FIG. 2F shows the user advancing the sensor applicator 102 toward the target monitoring location 222. Upon engaging the skin at the target monitoring location 222, the sheath 212 collapses into the housing 208, which allows the sensor control device 104 (FIGS. 2E and 2G) to advance into engagement with the skin. With the help of the sharp 220 (FIG. 2E), the sensor 110 (FIG. 2E) is advanced transcutaneously into the patient's skin at the target monitoring location 222.

FIG. 2G shows the user retracting the sensor applicator 102 from the target monitoring location, with the sensor control device 104 successfully attached to the user's skin. The adhesive patch 108 (FIG. 1) applied to the bottom of sensor control device 104 adheres to the skin to secure the sensor control device 104 in place. The sharp 220 (FIG. 2E) is automatically retracted when the housing 208 is fully advanced at the target monitoring location 222, while the sensor 110 (FIG. 2E) is left in position to measure analyte levels.

Figure 3A:
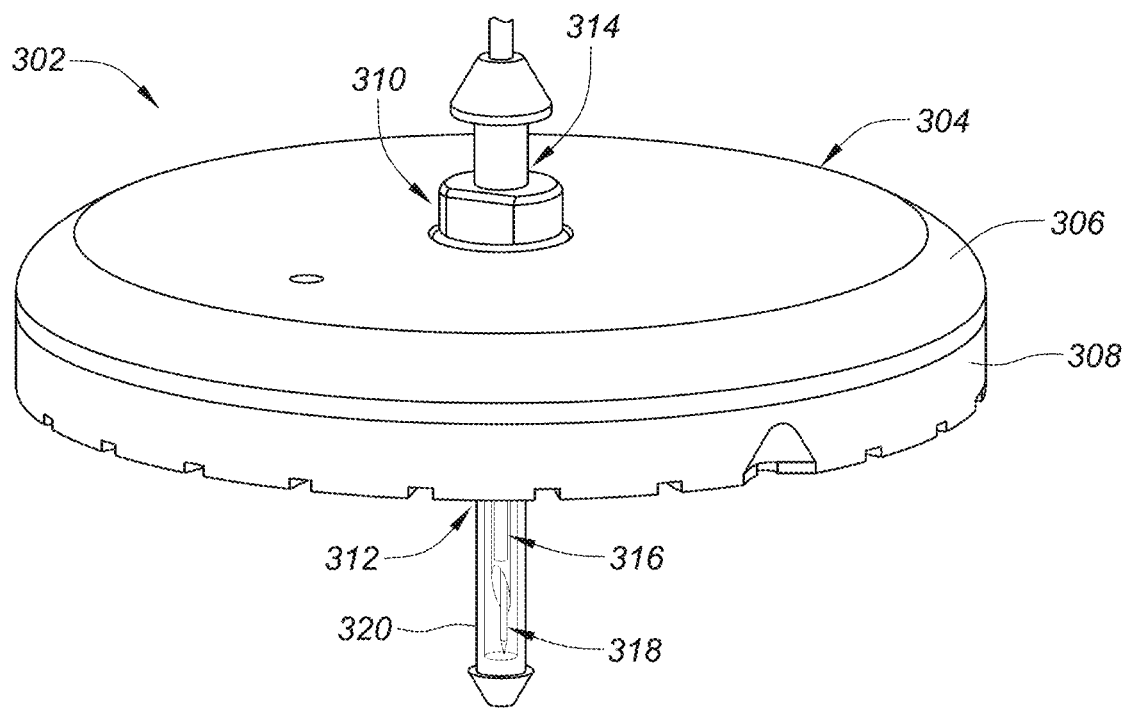
FIGS. 3A and 3B are isometric and side views, respectively, of an example sensor control device.
Figure 3B:
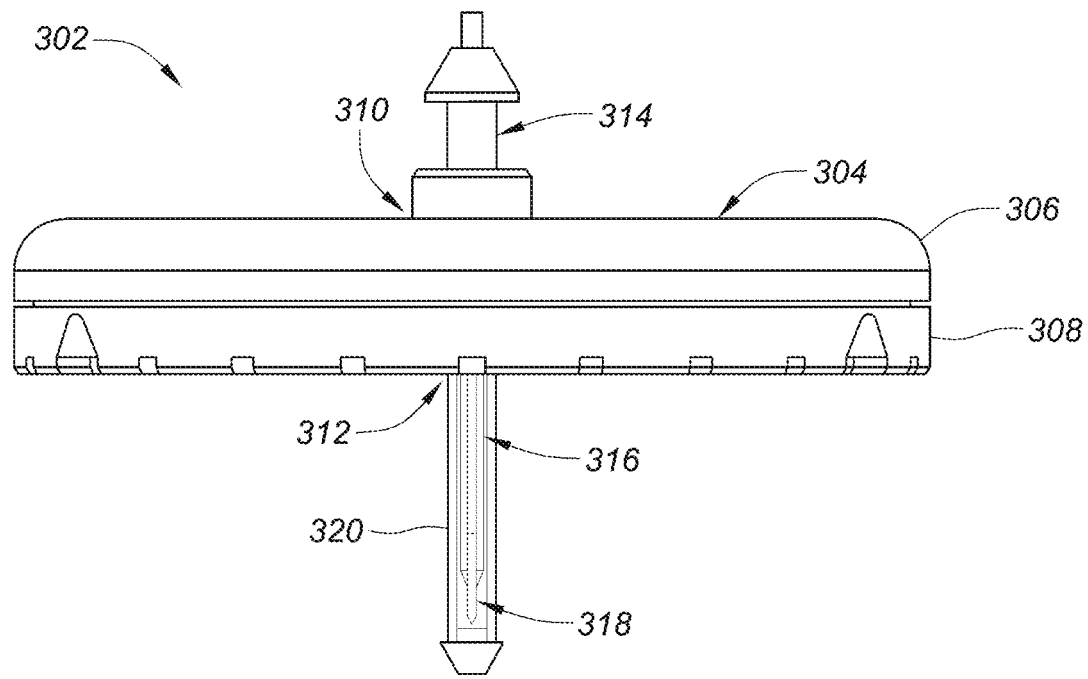

FIGS. 3A and 3B are isometric and side views, respectively, of an example sensor control device 302, according to one or more embodiments of the present disclosure. The sensor control device 302 (alternately referred to as a "puck") may be similar in some respects to the sensor control device 104 of FIG. 1 and therefore may be best understood with reference thereto. The sensor control device 302 may replace the sensor control device 104 of FIG. 1 and, therefore, may be used in conjunction with the sensor applicator 102 (FIG. 1), which delivers the sensor control device 302 to a target monitoring location on a user's skin.

The sensor control device 302, however, may be incorporated into a one-piece system architecture in contrast to the sensor control device 104 of FIG. 1. Unlike the two-piece architecture, for example, a user is not required to open multiple packages and finally assemble the sensor control device 302. Rather, upon receipt by the user, the sensor control device 302 is already fully assembled and properly positioned within the sensor applicator 102 (FIG. 1). To use the sensor control device 302, the user need only open one barrier (e.g., the cap 210 of FIG. 2B) before promptly delivering the sensor control device 302 to the target monitoring location.

As illustrated, the sensor control device 302 includes an electronics housing 304 that is generally disc-shaped and may have a circular cross-section. In other embodiments, however, the electronics housing 304 may exhibit other cross-sectional shapes, such as ovoid or polygonal, without departing from the scope of the disclosure. The electronics housing 304 may be configured to house or otherwise contain various electrical components used to operate the sensor control device 302.

The electronics housing 304 may include a shell 306 and a mount 308 that is matable with the shell 306. The shell 306 may be secured to the mount 308 via a variety of ways, such as a snap fit engagement, an interference fit, sonic welding, or one or more mechanical fasteners (e.g., screws). In some cases, the shell 306 may be secured to the mount 308 such that a sealed interface therebetween is generated. In such embodiments, a gasket or other type of seal material may be positioned at or near the outer diameter (periphery) of the shell 306 and the mount 308, and securing the two components together may compress the gasket and thereby generate a sealed interface. In other embodiments, an adhesive may be applied to the outer diameter (periphery) of one or both of the shell 306 and the mount 308. The adhesive secures the shell 306 to the mount 308 and provides structural integrity, but may also seal the interface between the two components and thereby isolate the interior of the electronics housing 304 from outside contamination. If the sensor control device 302 is assembled in a controlled environment, there may be no need to terminally sterilize the internal electrical components. Rather, the adhesive coupling may provide a sufficient sterile barrier for the assembled electronics housing 304.

The sensor control device 302 may further include a plug assembly 310 that may be coupled to the electronics housing 304. The plug assembly 310 may be similar in some respects to the plug assembly 207 of FIG. 2A. For example, the plug assembly 310 may include a sensor module 312 (partially visible) interconnectable with a sharp module 314 (partially visible). The sensor module 312 may be configured to carry and otherwise include a sensor 316 (partially visible), and the sharp module 314 may be configured to carry and otherwise include a sharp 318 (partially visible) used to help deliver the sensor 316 transcutaneously under a user's skin during application of the sensor control device 302. As illustrated, corresponding portions of the sensor 316 and the sharp 318 extend from the electronics housing 304 and, more particularly, from the bottom of the mount 308. The exposed portion of the sensor 316 may be received within a hollow or recessed portion of the sharp 318. The remaining portion of the sensor 316 is positioned within the interior of the electronics housing 304. The sensor control device 302 may further include a sensor preservation vial 320 that provides a preservation barrier surrounding and protecting the exposed portions of the sensor 316 and the sharp 318 from gaseous chemical sterilization.

Figure 4A:
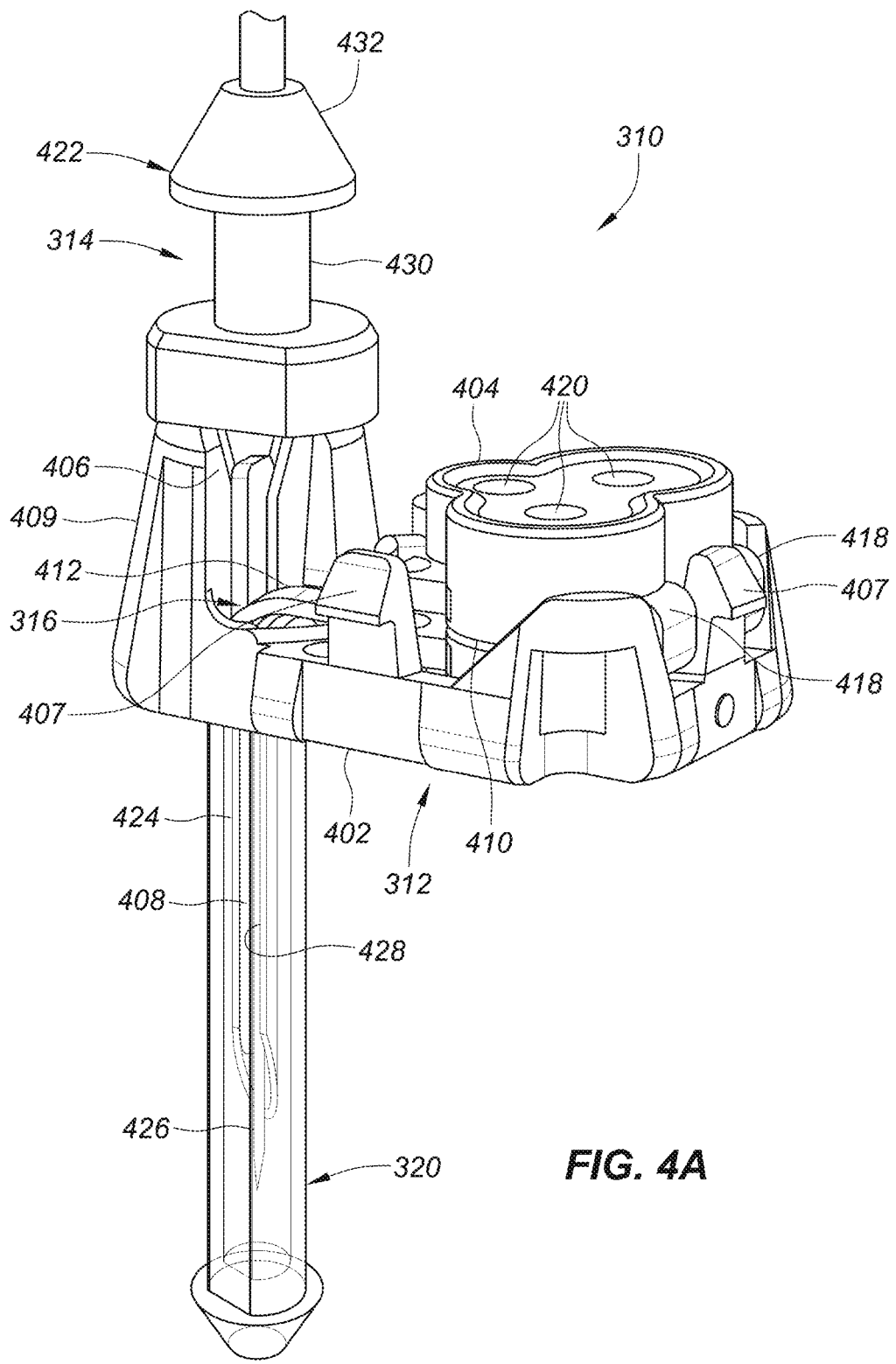
FIGS. 4A and 4B are isometric and exploded views, respectively, of the plug assembly of FIGS. 3A-3B.
Figure 4B:
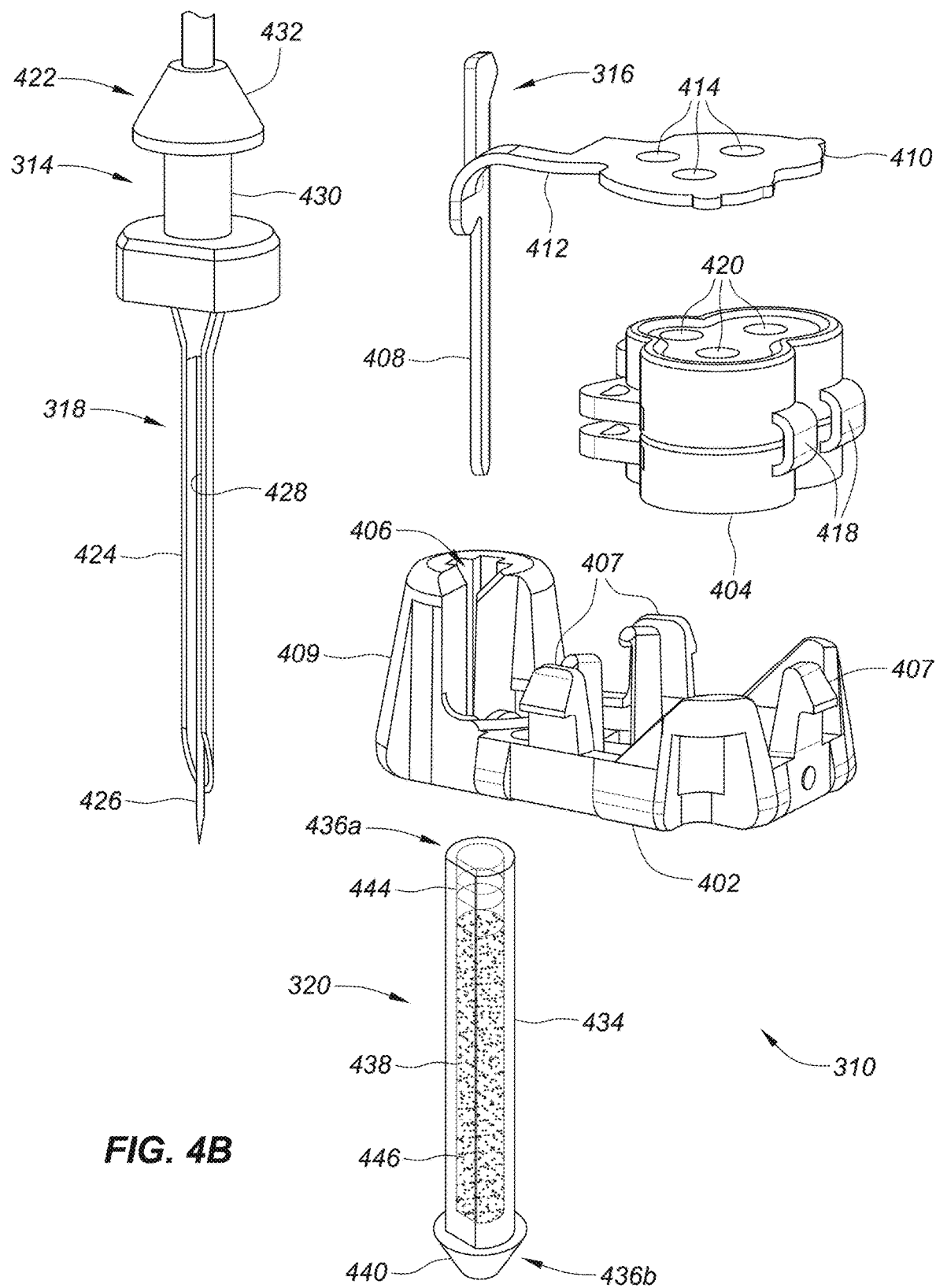

FIGS. 4A and 4B are isometric and exploded views, respectively, of the plug assembly 310, according to one or more embodiments. The sensor module 312 may include the sensor 316, a plug 402, and a connector 404. The plug 402 may be designed to receive and support both the sensor 316 and the connector 404. As illustrated, a channel 406 may be defined through a plug portion 409 to receive a portion of the sensor 316. The plug portion can be any shape, e.g., a frustoconical, round, oval, or other shaped portion. Moreover, the plug 402 may provide one or more deflectable arms 407 configured to snap into corresponding features provided on the bottom of the electronics housing 304 (FIGS. 3A-3B).

The sensor 316 includes a tail 408, a flag 410, and a neck 412 that interconnects the tail 408 and the flag 410. The tail 408 may be configured to extend at least partially through the channel 406 and extend distally from the plug 402. The tail 408 includes an enzyme or other chemistry or biologic and, in some embodiments, a membrane may cover the chemistry. In use, the tail 408 is transcutaneously received beneath a user's skin, and the chemistry included thereon helps facilitate analyte monitoring in the presence of bodily fluids.

The flag 410 may comprise a generally planar surface having one or more sensor contacts 414 (three shown in FIG. 4B) arranged thereon. The sensor contact(s) 414 may be configured to align with a corresponding number of compliant carbon impregnated polymer modules (tops of which shown at 420) encapsulated within the connector 404.

The connector 404 includes one or more hinges 418 that enables the connector 404 to move between open and closed states. The connector 404 is depicted in FIGS. 4A-4B in the closed state, but can pivot to the open state to receive the flag 410 and the compliant carbon impregnated polymer module(s) therein. The compliant carbon impregnated polymer module(s) provide electrical contacts 420 (three shown) configured to provide conductive communication between the sensor 316 and corresponding circuitry contacts provided within the electrical housing 304 (FIGS. 3A-3B). The connector 404 can be made of silicone rubber and may serve as a moisture barrier for the sensor 316 when assembled in a compressed state and after application to a user's skin.

The sharp module 314 includes the sharp 318 and a sharp hub 422 that carries the sharp 318. The sharp 318 includes an elongate shaft 424 and a sharp tip 426 at the distal end of the shaft 424. The shaft 424 may be configured to extend through the channel 406 and extend distally from the plug 402. Moreover, the shaft 424 may include a hollow or recessed portion 428 that at least partially circumscribes the tail 408 of the sensor 316. The sharp tip 426 may be configured to penetrate the skin while carrying the tail 408 to put the active chemistry present on the tail 408 into contact with bodily fluids.

The sharp hub 422 may include a hub small cylinder 430 and a hub snap pawl 432, each of which may be configured to help couple the plug assembly 310 (and the entire sensor control device 302) to the sensor applicator 102 (FIG. 1).

With specific reference to FIG. 4B, the preservation vial 320 may comprise a generally cylindrical and elongate body 434 having a first end 436a and a second end 436b opposite the first end 436a. The first end 436a may be open to provide access into an inner chamber 438 defined within the body 434. In contrast, the second end 436b may be closed and may provide or otherwise define an enlarged head 440. The enlarged head 440 exhibits an outer diameter that is greater than the outer diameter of the remaining portions of the body 434. In other embodiments, however, the enlarged head 440 may be positioned at an intermediate location between the first and second ends 436a,b.

Figure 4C:
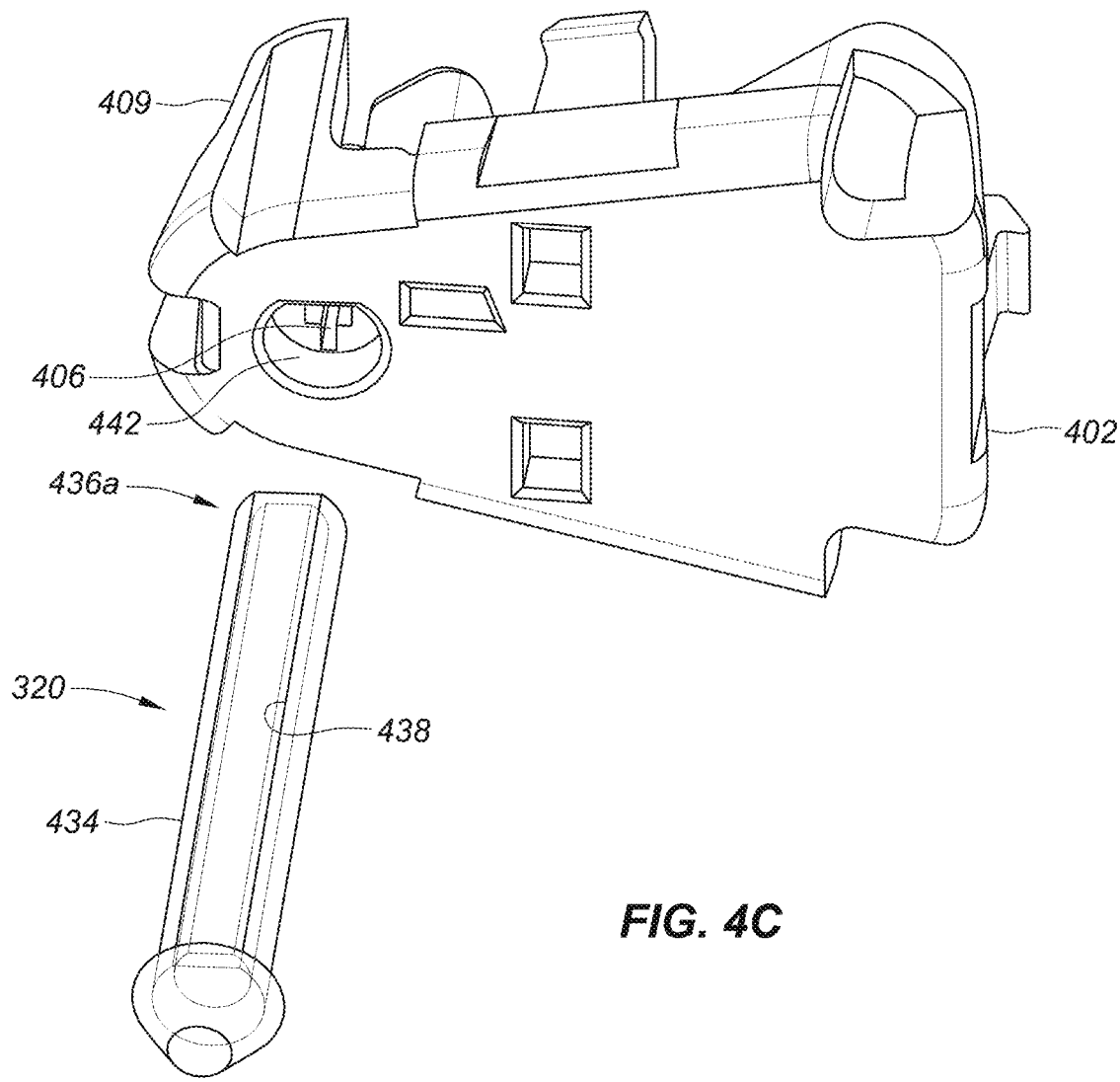
FIG. 4C is an exploded isometric bottom view of the plug and a preservation vial.

FIG. 4C is an exploded isometric bottom view of the plug 402 and the preservation vial 320. As illustrated, the plug 402 may define an aperture 442 configured to receive the preservation vial 320 and, more particularly, the first end 436a of the body 434. The channel 406 may terminate at the aperture 442 such that components extending out of and distally from the channel 406 will be received into the inner chamber 438 when the preservation vial 320 is coupled to the plug 402. Additional details about the preservation vial 320 can be found in International Application No. PCT/US19/32848, filed Jun. 10, 2019, which is hereby expressly incorporated by referenced in its entirety for all purposes.

The plug assembly 310 may be subjected to radiation sterilization to properly sterilize the sensor 316 and the sharp 318. Suitable radiation sterilization processes include, but are not limited to, electron beam (e-beam) irradiation, gamma ray irradiation, X-ray irradiation, or any combination thereof. In some embodiments, the plug assembly 310 may be subjected to radiation sterilization prior to coupling the preservation vial 320 to the plug 402. In other embodiments, however, the plug assembly 310 may be sterilized after coupling the preservation vial 320 to the plug 402. In such embodiments, the body 434 of the preservation vial 320 and the preservation fluid 446 may comprise materials and/or substances that permit the propagation of radiation therethrough to facilitate radiation sterilization of the distal portions of the sensor 316 and the sharp 318.

Figure 5A:
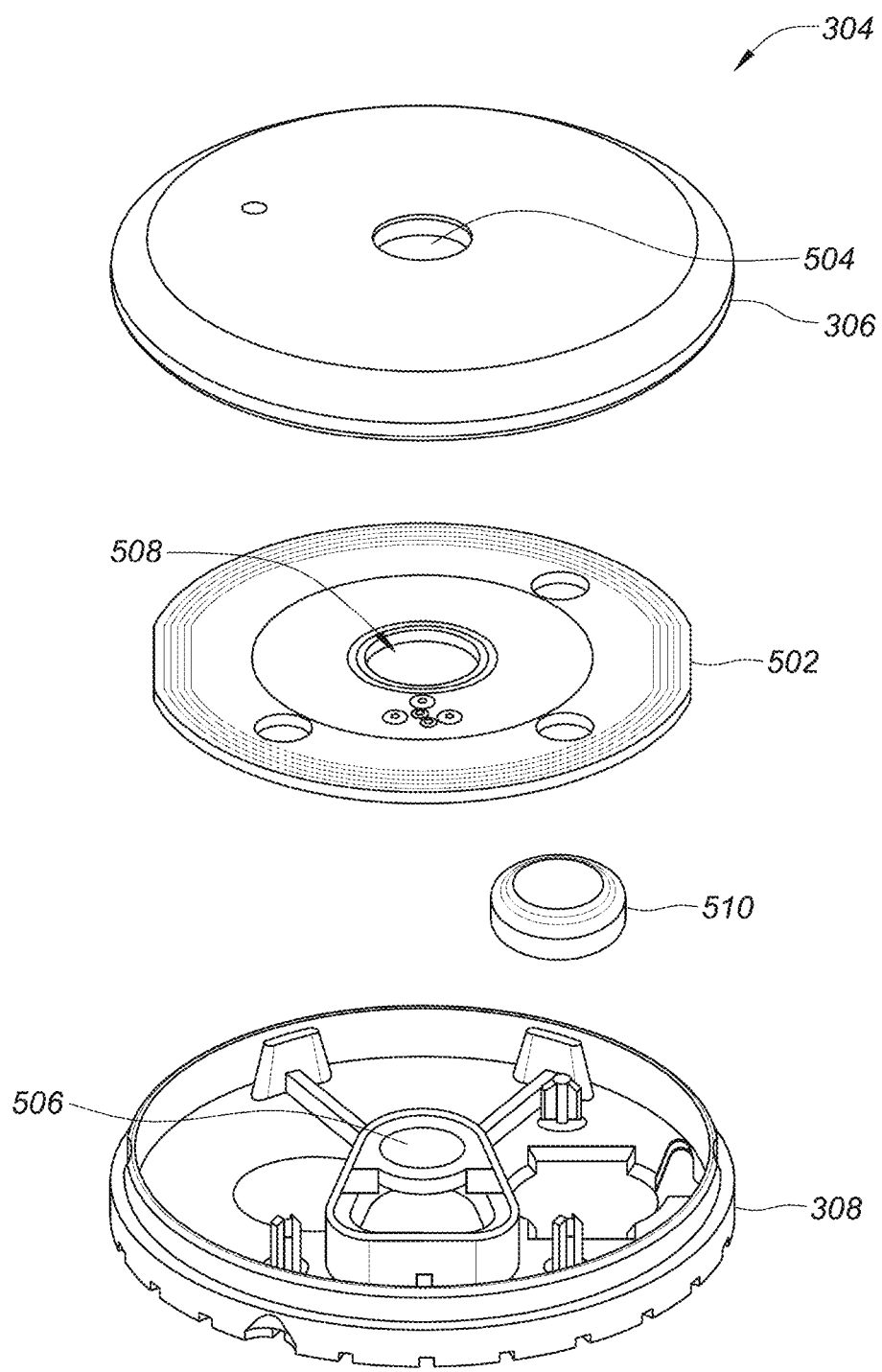
FIGS. 5A and 5B are exploded and bottom isometric views, respectively, of the electronics housing of FIGS. 3A-3B.
Figure 5B:
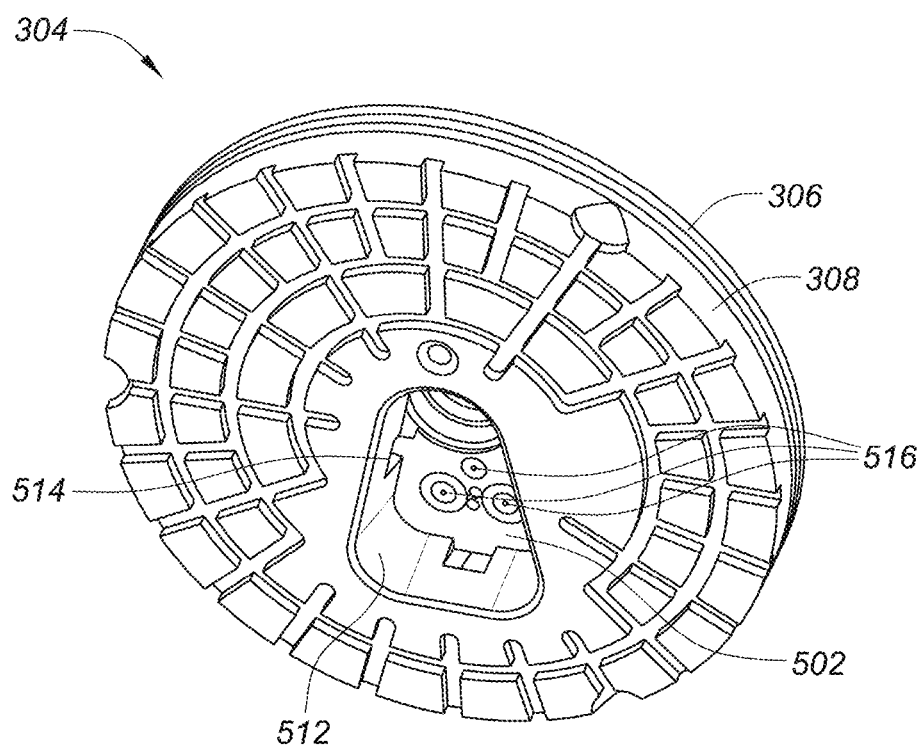

FIGS. 5A and 5B are exploded and bottom isometric views, respectively, of the electronics housing 304, according to one or more embodiments. The shell 306 and the mount 308 operate as opposing clamshell halves that enclose or otherwise substantially encapsulate the various electronic components of the sensor control device 302 (FIGS. 3A-3B).

A printed circuit board (PCB) 502 may be positioned within the electronics housing 304. A plurality of electronic modules (not shown) may be mounted to the PCB 502 including, but not limited to, a data processing unit, resistors, transistors, capacitors, inductors, diodes, and switches. The data processing unit may comprise, for example, an application specific integrated circuit (ASIC) configured to implement one or more functions or routines associated with operation of the sensor control device 302. More specifically, the data processing unit may be configured to perform data processing functions, where such functions may include but are not limited to, filtering and encoding of data signals, each of which corresponds to a sampled analyte level of the user. The data processing unit may also include or otherwise communicate with an antenna for communicating with the reader device 106 (FIG. 1).

As illustrated, the shell 306, the mount 308, and the PCB 502 each define corresponding central apertures 504, 506, and 508, respectively. When the electronics housing 304 is assembled, the central apertures 504, 506, 508 coaxially align to receive the plug assembly 310 (FIGS. 4A-4B) therethrough. A battery 510 may also be housed within the electronics housing 304 and configured to power the sensor control device 302.

In FIG. 5B, a plug receptacle 512 may be defined in the bottom of the mount 508 and provide a location where the plug assembly 310 (FIGS. 4A-4B) may be received and coupled to the electronics housing 304, and thereby fully assemble the sensor control device 302 (FIG. 3A-3B). The profile of the plug 402 (FIGS. 4A-4C) may match or be shaped in complementary fashion to the plug receptacle 512, and the plug receptacle 512 may provide one or more snap ledges 514 (two shown) configured to interface with and receive the deflectable arms 407 (FIGS. 4A-4B) of the plug 402. The plug assembly 310 is coupled to the electronics housing 304 by advancing the plug 402 into the plug receptacle 512 and allowing the deflectable arms 407 to lock into the corresponding snap ledges 514. When the plug assembly 310 (FIGS. 4A-4B) is properly coupled to the electronics housing 304, one or more circuitry contacts 516 (three shown) defined on the underside of the PCB 502 may make conductive communication with the electrical contacts 420 (FIGS. 4A-4B) of the connector 404 (FIGS. 4A-4B).

Inactive components of the sensor assembly can be used to present bioactive substances to the surface and the area adjacent to and/or surrounding the extracorporeal portion of the sensor(s), and optionally, within the implant sites. For example, inactive components of the sensor assembly can be made with antimicrobial properties or can be made to include antimicrobial agents. This could accomplish sustained delivery of antimicrobial agents from the inactive components to the surface of the sensor assembly and the adjacent areas, such as the skin. The sustained delivery could result in controlled and long-lasting delivery of antimicrobial agents from the non-active components. Sensor systems that include inactive components containing antimicrobial agents could be self-preserving.

The manufacture of inactive components with antimicrobial properties could have many benefits. These include improved sensor longevity through the suppression of microbial expansion and/or invasion. Sensor accuracy could also be improved under unfavorable sensing conditions, such as the presence of an infection. This multi-tiered technique could also reduce immune cell infiltration to the implant site. Inactive components with antimicrobial properties could also inhibit microorganisms and eliminate infection-related immune response from the host, which would lead to high immune cell density and tissue encapsulations. The sensor could also be used in a compromised site, e.g., an infected site, skin, or wound bed. An antimicrobial agent could also be selected that has minimal or no interference on sensor functionality.

Sputter coating could be used to deliver antimicrobials to inactive components for improved sensor function. Moreover, introduction of air or oxygen during sputtering may produce oxide coatings with increased or improved antimicrobial properties, as compared to coatings with a lower amount of oxidation. Antimicrobial agents could be compounded with raw materials or formed in an impregnation process to form antimicrobial leaching non-active or inactive components with improved sensor function.

Figure 6A:
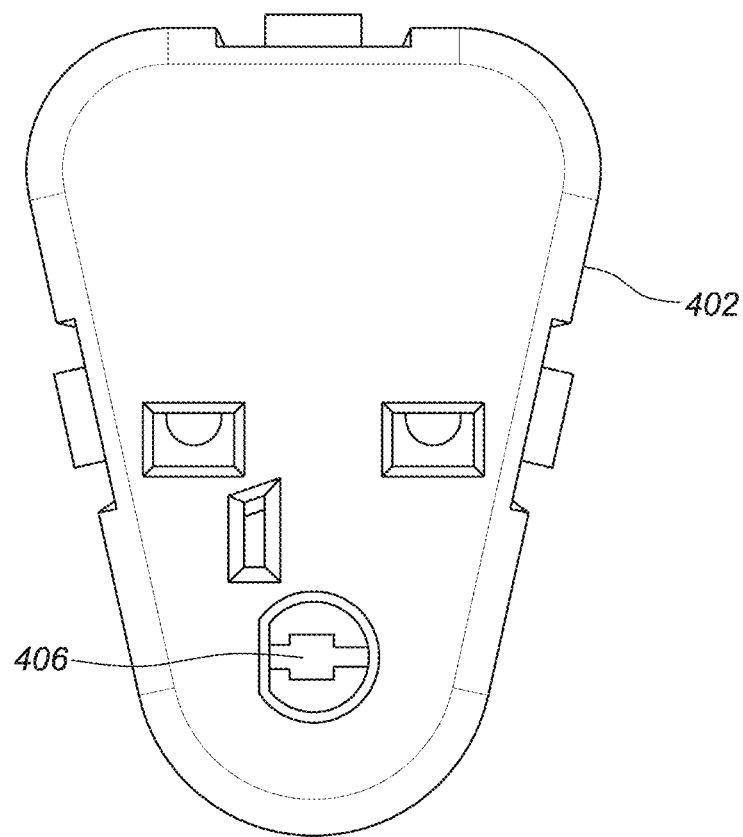
FIG. 6A is a bottom view of a plug assembly.
Figure 6B:
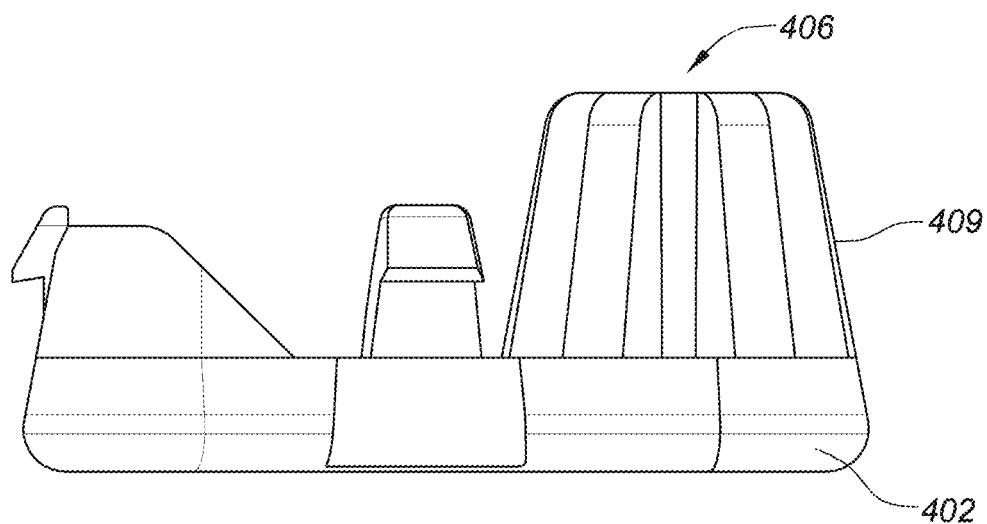
FIG. 6B is a side view of a plug assembly.
Figure 6C:
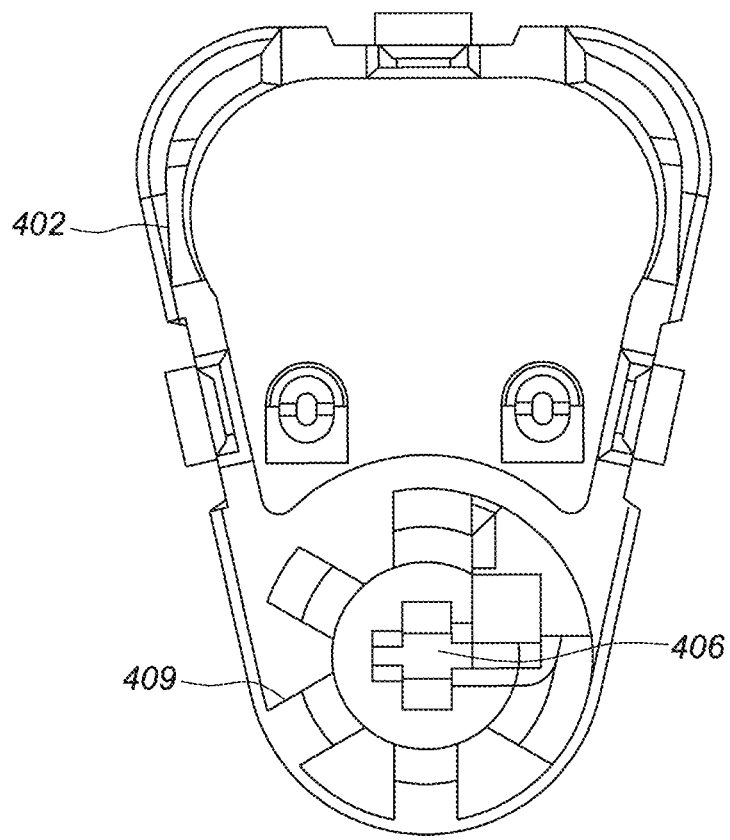
FIG. 6C is a top view of a plug assembly.

Inactive components that could be manufactured to include an antimicrobial agent include parts of the sensor system that are exposed to the environment once assembled. Inactive components that may include antimicrobial agents include elements of the shell 306 and plug assembly 310. These include, but are not limited to, the shell 306 (see, e.g., FIG. 5A), and in particular, the upper facing surface and outer perimeter lip of shell 306; the mount 308 (see, e.g., FIG. 5B), in particular, the lower or skin-facing surface and lower perimeter lip of mount 308; the plug 402, in particular the lower or skin-facing surface of plug 402 (see, e.g., FIGS. 4C and 6A), the outward facing surface of the plug portion 409 (see, e.g., FIGS. 4B and 6B), the upward facing surface of the plug portion 409 (see, e.g., FIGS. 4B and 6C), and the exterior surface and interior surface (channel 406) of the plug portion 409 (see, e.g., FIGS. 4B, 6B, and 6C). While shown in the figures as having a frustoconical shape, the plug portion 409 can be any shape, e.g., frustoconical, round, oval, or other shapes.

Antimicrobial and/or microstatic substances or agents that can be utilized to inhibit microorganism-related disturbances include, but are not limited to, silver, copper, zinc, and combinations thereof, such as silver on copper, copper on silver, and oxides thereof. These antimicrobial and/or microstatic substances or agents can be blended into the bulk material and incorporated throughout the component, layered via overmolding, applied as a thin layer to the surface(s) (e.g., through sputter coating), or through a variety of impregnation methods that introduce the antimicrobial and/or microstatic substances in an outer region of the inactive component. Inactive components may also be first coated with a thin layer of another metal or material, such as titanium, to increase adhesion of the antimicrobial and/or microstatic substances.

In some embodiments, metal-based antimicrobial compounds may be particularly useful for imparting the antimicrobial qualities to inactive components (shell and plug assembly). These metal-based antimicrobial compounds may be metal ion, a metal oxide, metal salts, metal coordination compounds including chelates, and the like. Specific examples of suitable metal-based antimicrobial compounds may include, but are not limited to, silver, sliver chloride, silver-silver chloride, silver iodide, silver carbonate, silver nitrate, copper, copper sulfate, cupric oxalate, silver oxalate, magnetite, gold, gallium, platinum, palladium, titanium dioxide, zinc oxide, magnesium oxide, silicon dioxide, iron oxide, carbon dioxide, copper oxide, nitric oxide, carbon nanotubes, and the like (e.g., other antimicrobial heavy metal ions and/or metal oxides), any alloys thereof, any salts thereof, any coordination complexes and/or chelates thereof, any combination thereof, and any combination thereof in addition to one or more of the antimicrobial compounds described herein.

In some embodiments, the metal-based antimicrobials may be metal-containing nanoparticles, such as impregnated or made whole from the antimicrobial compound, including as non-limiting examples, any nanoparticles comprised of the metal-based antimicrobial compounds described herein.

In some embodiments, a layer of metal-based antimicrobials can be applied via sputtering. In some embodiments, increasing the oxygen content in the sputtering process increases the amount of metal oxide in the layer. The method may include a step of sputtering a metal layer on a substrate in a first atmosphere consisting essentially of an inert gas. Alternatively or in addition to, the method includes forming a metal oxide-containing layer by sputtering a metal in a second atmosphere comprising a mixture of an inert gas and an oxidant. The oxidant may make up between about 0.5% and 100% of the second atmosphere, alternatively between about 5% and 95%, alternatively between about 15% and 60%, alternatively between about 20% and 60%, alternatively between about 30% and 60%, alternatively between about 40% and 60%, alternatively between about 50% and 60% by partial pressure. The oxidant may be air, oxygen, ozone, or water.

The inactive components may include a coating containing a portion of metal oxide. In one embodiment, the coating contains at least 2% metal oxide, alternatively at least 5% metal oxide, alternatively at least 10% metal oxide, alternatively at least 20% metal oxide, alternatively between about 30% and about 40% metal oxide, alternatively between about 2% and about 20% metal oxide, alternatively between about 10% and about 30% metal oxide by weight.

The metal or metal oxide layers may have a thickness of at least about 500 Å, alternatively about 750 Å, alternatively between about 400 Å and about 1000 Å, alternatively between about 500 Å and about 800 Å, alternatively between about 1 μm and about 10 μm, alternatively between about 1 μm and about 10 μm, alternatively between about 5 μm and about 10 μm, alternatively between about 500 Å and about 10 μm.

In other embodiments, the inactive components can be molded with a material containing a metal, a metal salt, or a metal oxide. For example, the inactive components could be molded with a polycarbonate containing silver and zinc salts, alternatively copper and zinc salts, alternately silver and copper salts, alternatively silver and zinc oxides, alternatively copper and zinc oxides, alternately silver and copper oxides.

Accordingly, certain sensor control devices of the present disclosure may comprise: an electronics housing comprising an upper shell matable to a lower mount having a skin-facing surface; and a plug assembly coupled to the electronics housing and including a sensor module that has a sensor and a sharp module comprising a sharp, the plug assembly comprising a base having a skin-facing surface and a plug portion comprising a lumen therethrough, wherein at least a portion of a surface of the electronics housing or the plug assembly comprises an antimicrobial agent. The plug portion can be any shape, including frustoconical, round, oval, or other shapes.

In one embodiment, the surfaces that may include the antimicrobial agent includes, but is not limited to, the upper shell of the electronics housing, and in particular an upper facing surface of the upper shell and the outer perimeter of the upper shell, the skin-facing surface of the lower mount, the skin-facing surface of the base of the plug, an outward facing surface of the plug portion, an upward facing surface of the plug portion, and an exterior surface of the plug portion. The plug portion can be any shape, including frustoconical, round, oval, or other shapes.

In another embodiment, the medical device may comprise: a housing having a skin-facing surface, and a layer containing a metal oxide adjacent the skin-facing surface. The layer may be configured to be in contact with a patient's skin and may comprise at least about 5% metal oxide by weight. The medical device may be configured to be in contact with the patient's skin for at least 10 days, alternatively at least 12 days, alternatively between about 10 days to about 14 days, alternatively for at least a few days, alternatively for at least a week, alternatively for at least a few weeks.

In one embodiment, the antimicrobial agent may be a metal and/or a metal oxide, such as silver, copper, zinc, and combinations thereof. For example, the antimicrobial agent may include silver and copper, e.g., silver on copper and copper on silver.

In one embodiment, the antimicrobial agent may be contained in a coating applied to the surface(s) of the sensor control device. Alternatively, the antimicrobial agent may be blended into a bulk material used to make the inactive components of the sensor control device. Alternatively, the antimicrobial agent may be incorporated throughout a material used to make the inactive components of the sensor control device. Alternatively, the antimicrobial agent may be impregnated into the at least the portion of the surface of the inactive components of the sensor control device. Alternatively, the antimicrobial agent may be applied onto the surface of the inactive components of the sensor control device via overmolding. Alternatively, the antimicrobial agent may be applied onto the surface of the inactive components of the sensor control device via sputter coating to form a layer containing an antimicrobial agent.

In one embodiment, the antimicrobial agent is contained in at least one layer that is applied onto a surface of the inactive components, e.g., the electronics housing or the plug assembly. Alternatively, the antimicrobial agent is contained in at least two layers, alternatively at least three layers, alternatively at least four layers that are applied onto a surface of the inactive components.

In another embodiment, a method includes the step of applying a layer containing an antimicrobial agent onto a surface of a sensor control device, the sensor control device comprising an electronics housing comprising an upper shell having an outer perimeter lip, the upper shell matable to a lower mount having a skin-facing surface; and a plug assembly coupled to the electronics housing and including a sensor module that has a sensor and a sharp module comprising a sharp, the plug assembly comprising a base having a skin-facing surface and a plug portion having a lumen therethrough. The surface of the sensor control device to which the layer containing the antimicrobial agent is applied may be at least one of the upper shell, the outer perimeter lip, the skin-facing surface of the lower mount, the skin-facing surface of the base, and the plug portion. The plug portion can be any shape, including frustoconical, round, oval, or other shapes.

In another embodiment, a method includes the step of sputtering a layer containing a metal onto a surface of a sensor control device, the sensor control device comprising an electronics housing comprising an upper shell having an outer perimeter lip, the upper shell matable to a lower mount having a skin-facing surface; and a plug assembly coupled to the electronics housing and including a sensor module that has a sensor and a sharp module comprising a sharp, the plug assembly comprising a base having a skin-facing surface and a plug portion having a lumen therethrough. The surface of the sensor control device to which the layer containing the antimicrobial agent is sputtered may be at least one of the upper shell, the outer perimeter lip, the skin-facing surface of the lower mount, the skin-facing surface of the base, and the plug portion. The plug portion can be any shape, including frustoconical, round, oval, or other shapes.

In one embodiment, the metal may be silver, copper, zinc, or combinations thereof.

In one embodiment, the metal is sputtered onto the surface in an atmosphere comprising an inert gas and an oxidant. The inert gas may be Argon and the oxidant may be air or oxygen.

To facilitate a better understanding of the disclosure herein, the following examples of various representative embodiments are given. In no way should the following examples be read to limit, or to define, the scope of the invention.

EXAMPLES

Example 1: Zone of Inhibition Testing

Activity of the coatings against the relevant pathogen *P. aeruginosa* (PA; ATCC 27317) was evaluated using zone of inhibition (ZOI) assays. Bacteria were grown overnight at 37° C. in tryptic soy broth (TSB, MP Biomedicals, USA). *P. aeruginosa* overnight growth was diluted at 1:50 for *P. aeruginosa* in TSB, and 100.0 µL of these solutions were spread on 100×15 mm tryptic soy agar plates. Samples were placed with coated surface down, bringing the coating in direct contact with inoculated agar during lawn formation. These plates were incubated for 24 hours at 37° C. and photographed.

Figure 7C:
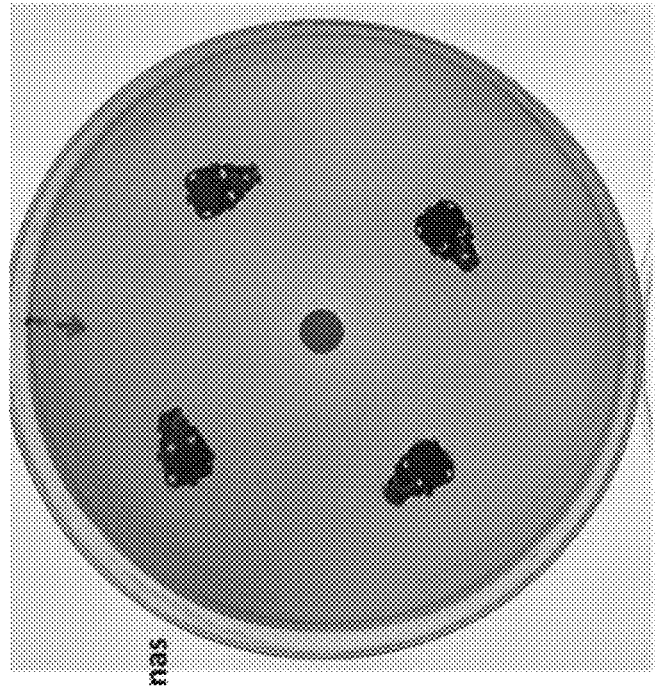
FIGS. 7B and 7C show the results of zone of inhibition testing using *Pseudomonas aeruginosa*.
Figure 7A:
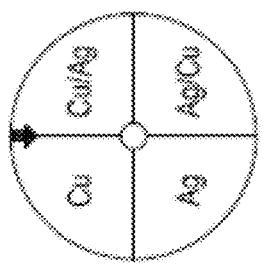
FIG. 7A is a diagram of a plate showing the different coatings in FIGS. 7B and 7C.
Figure 7B:
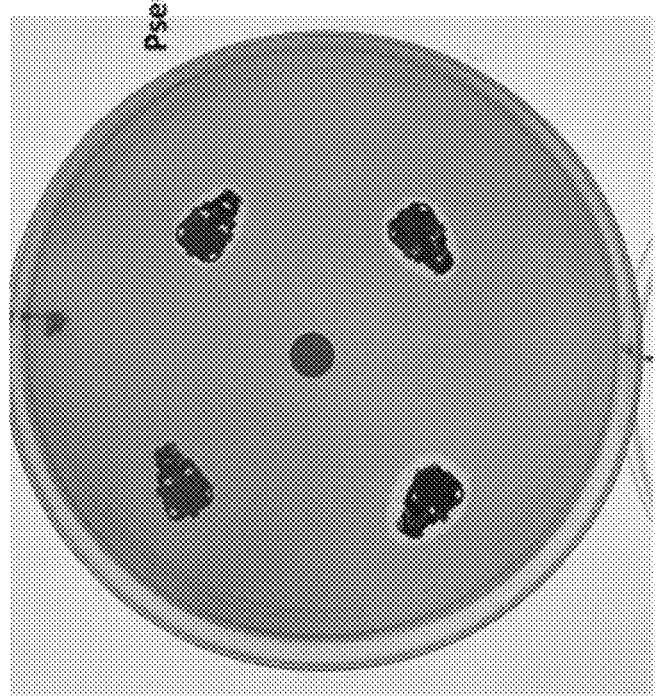

As seen in FIG. 7A, the coatings that were tested were (clockwise from top left) copper, silver on copper, copper on silver, and silver. Sputter coated surfaces were first prepped with a thin layer of titanium via sputtering to increase adhesion. The coatings in the plate shown in FIG. 7B have a higher degree of oxide than the coatings in the plate shown in FIG. 7C. As seen from FIGS. 7B and 7C, there was a greater zone of inhibition (lighter region surrounding the coatings) for the coatings with a higher degree of oxide as compared to the lower degree of oxide coatings.

Zone of inhibition testing is also being done on methicillin-resistant *S. aureus* (MRSA) (ATCC #33591), *S. epidermidis* (ATCC #12228), *E. faecalis* (ATCC #4082); *S. pyogenes* (ATCC #19615), *P. aeruginosa* (ATCC #27317); *P. acnes* (ATCC #6919), and methicillin-susceptible *S. aureus*.

Example 2: Effect of Additional Oxidation on the Appearance of Plug Assemblies The lower surfaces of the plug assemblies were coated with titanium, followed by silver on copper (FIG. 8A) and copper on silver (FIG. 8B). The titanium layer was added to increase adhesion of the silver and copper coatings.

Figure 8A:
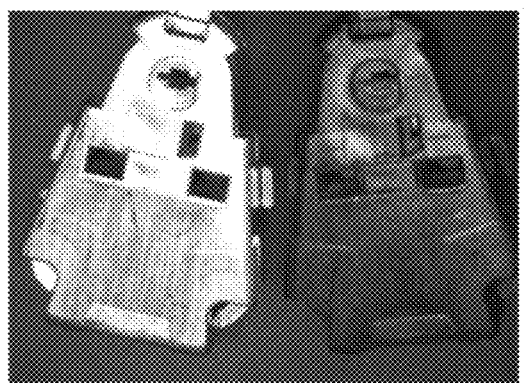
FIGS. 8A and 8B show the effect of different oxidation in coatings on the bottom of plug assemblies.
Figure 8B:
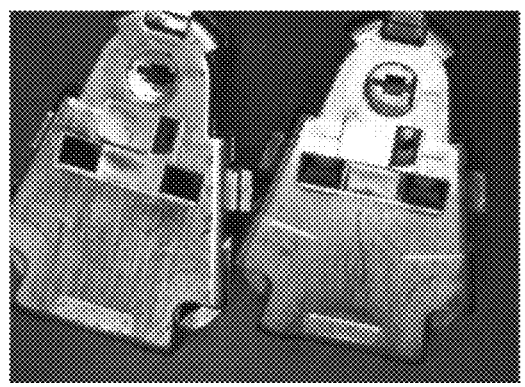

As seen in FIGS. 8A and 8B, the effect of additional oxidation is also evident on the appearance of the bottom surfaces of plug assemblies. FIG. 8A shows silver on copper and FIG. 8B shows copper on silver coatings.

Sputter-coated surfaces were first prepped with a thin layer of titanium via sputtering to increase adhesion. A titanium layer was deposited on the skin-facing surface of the plug assembly and a layer containing a metal oxide was sputtered on top of the titanium layer.

Example 3: Bacteria Adhesion/Biofilm Formation Testing

Figure 9A:
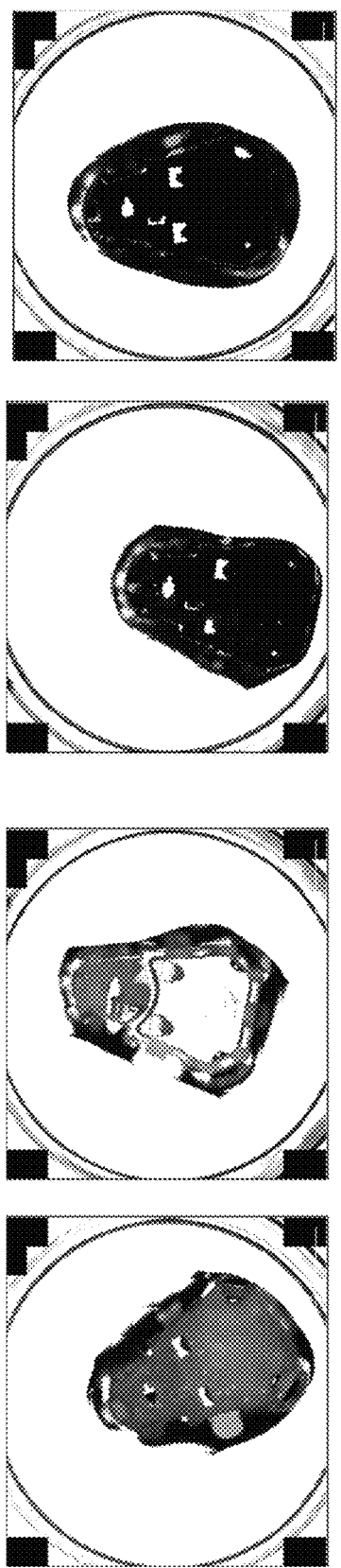
FIG. 9A are live dead images for *P. aeruginosa* resulting from Bacteria Adhesion/Biofilm Formation Testing.
Figure 9A:
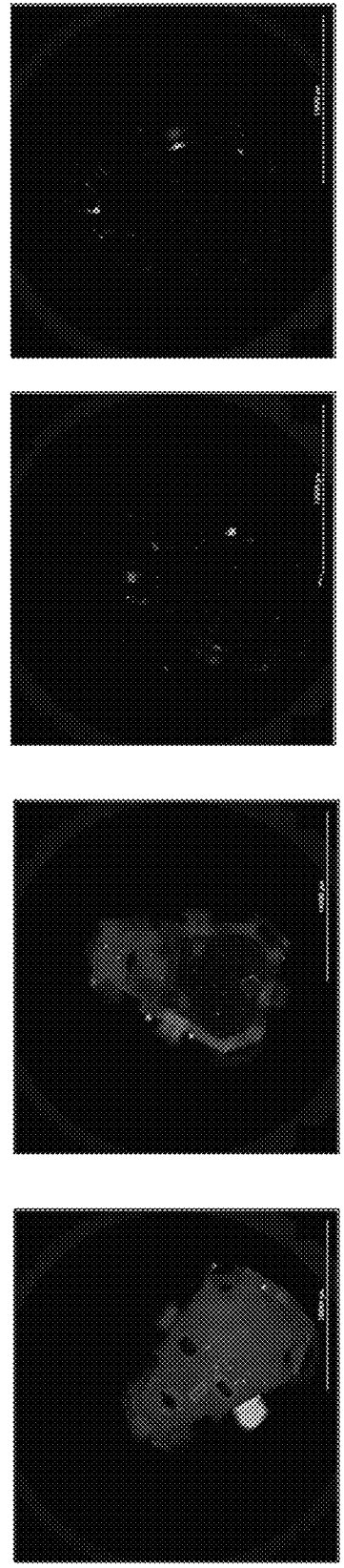
Figure 9B:
FIG. 9B are live dead images for *S. aureus* resulting from Bacteria Adhesion/Biofilm Formation Testing.
Figure 9B:
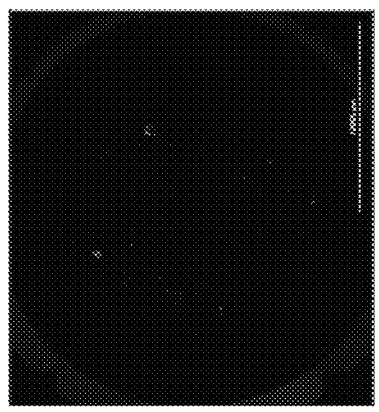
Figure 9B:
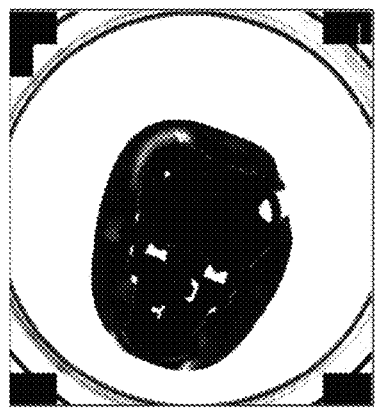
Figure 9B:
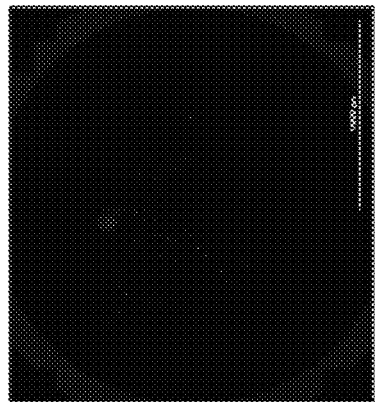
Figure 9B:
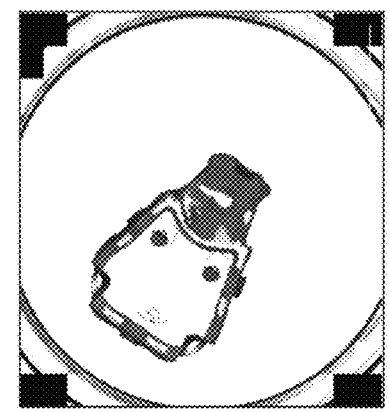
Figure 9B:
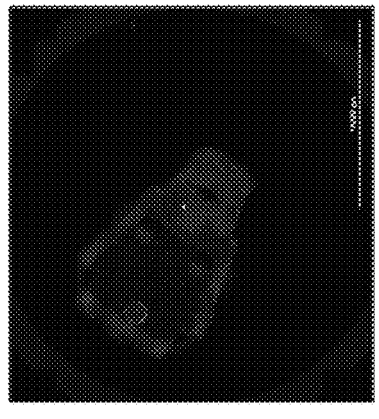
Figure 9B:
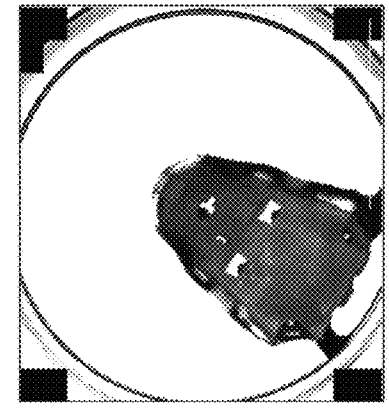
Figure 9B:
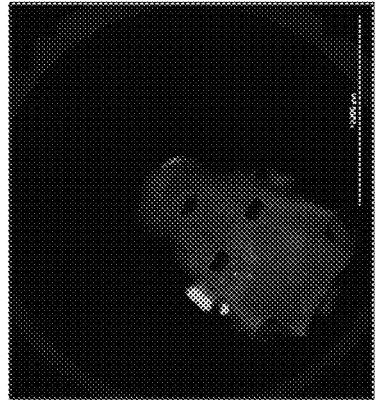

Samples are placed in inoculation media for a predetermined time (varies for each strain). After time has elapsed, samples are retrieved from the inoculum and labeled with Live/Dead Stain. A fluorescent microscope is then used to image the surfaces and observe attached CFUs and biofilms. FIG. 9A depicts the results for *P. aeruginosa* and FIG. 9B shows the results for *S. aureus*.

Bacteria adhesion and biofilm formation testing is being done on *P. aeruginosa* (ATCC #27317), *S. aureus* (MRSA) (ATCC #33591), *S. epidermidis* (ATCC #12228), *E. faecalis* (ATCC #4082); *S. pyogenes* (ATCC #19615), *P. aeruginosa* (ATCC #27317); *P. acnes* (ATCC #6919), and methicillin-susceptible *S. aureus* (UAMS-1).

Example 4: Log Reduction Testing (AKA Kill Assay (ISO 22196))

ISO 22196, which specifies a method for evaluating the antibacterial activity of non-porous surfaces in which surfaces are tested using a liquid bacterial culture, was also used to test the coatings. Bacterial suspensions were prepared in different dilutions. The plug surface of interest in these experiments was the skin-facing side (the same face of the plugs that were sputter coated). The groups of plugs included production plugs (control) and three experimental groups: (1) Ag-doped resin molded plugs, (2) high oxide Ti—Ag/Cu sputter coated plugs, and (3) high oxide Ti—Cu/Ag sputter coated plugs. The Ag-doped resin molded plugs were identical in shape and size to that of control plugs and were injection molded using WithStand antimicrobial resin (PolyOne; Avon Lake, OH). The resin was doped with a silver salt and could release silver ions. High oxide Cu and Ag sputter coated plugs were prepared as described previously in the application. Plugs were mounted in a custom holding device to such that the surface of interest faced up and was level with ground (see images). Experiments were run with plugs in mounts.

Twenty four-hour expansion/kill tests based on ISO 22196 were conducted, recovered CFUs were expanded 24 hours and counted to determine the effects. *P. aeruginosa* and *S. aureus* were independently inoculated onto the surfaces of plugs with $3\times10^4$ and $2\times10^4$ CFUs, respectively, in culture media. A glass coverslip was placed over the plug surface, producing an even distribution of bacteria over the surface of the plugs. Specimens were allowed to culture overnight. After overnight culture, specimens were either subjected to Live/Dead staining and imaging or subjected to a bacteria recovery and counting procedure. Bacteria recovery was conducted by sonicating the plugs in media. Total number of CFUs per plug was determined using a particle counter.

Figure 10A:
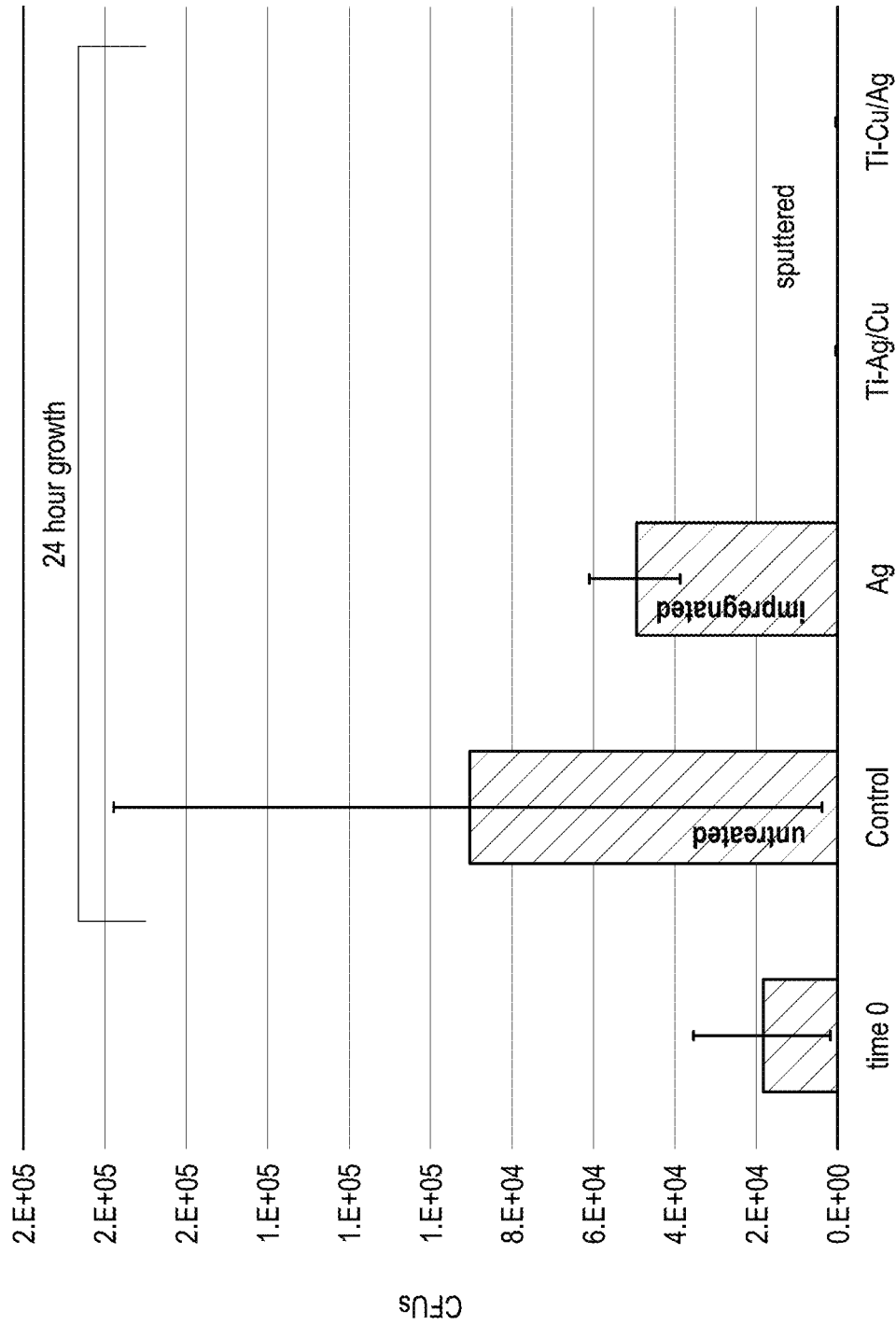
FIG. 10A show results from an ISO 22196-based kill assay for *S. aureus*.
Figure 10B:
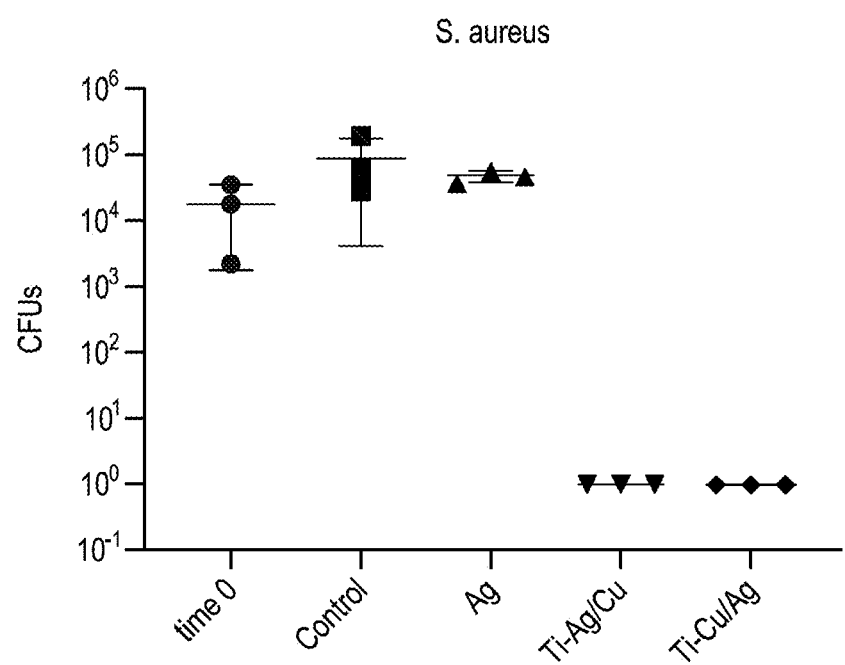
FIG. 10B show results from an ISO 22196-based kill assay for *S. aureus*.
Figure 10C:
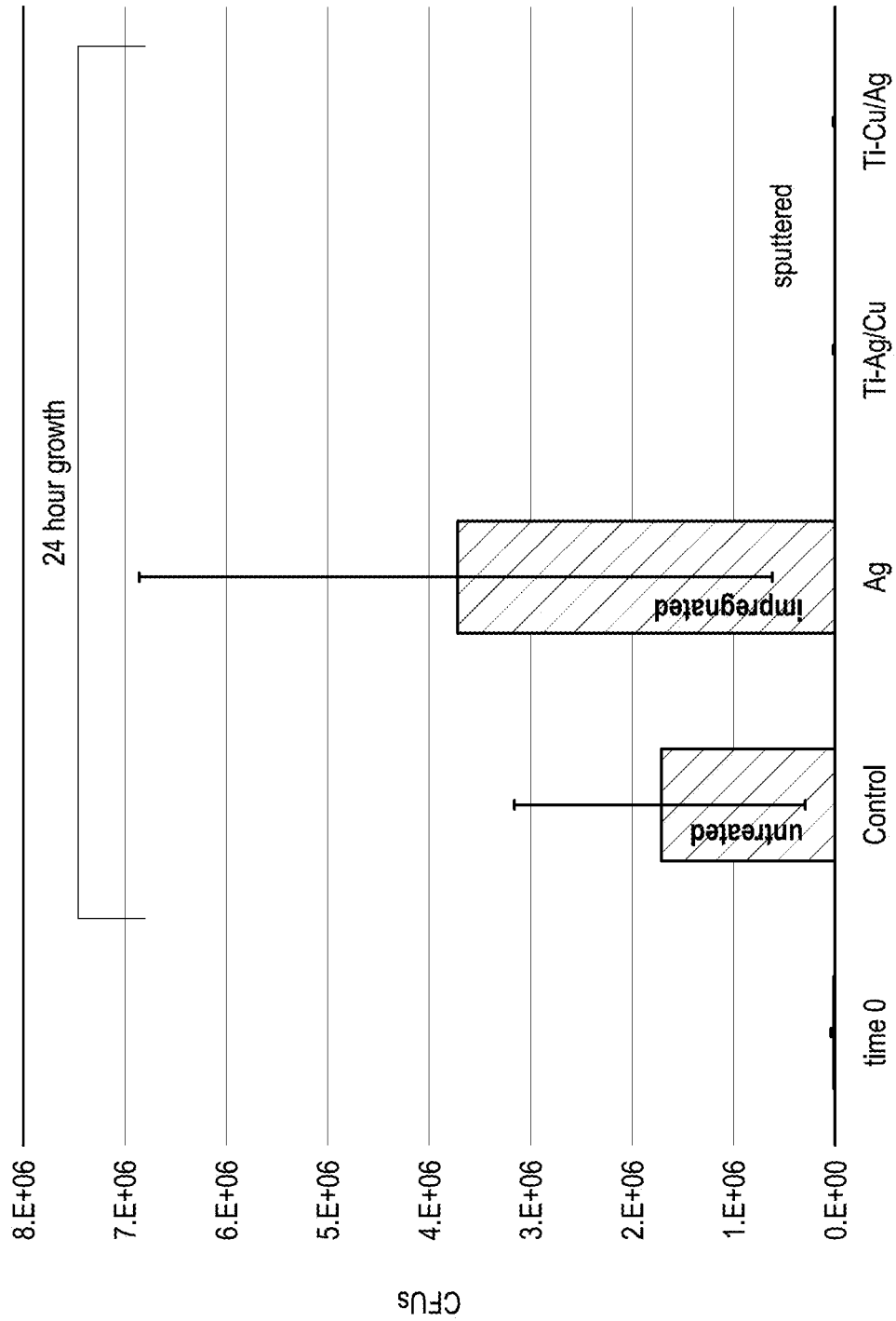
FIG. 10C show results from an ISO 22196-based kill assay for *P. aeruginosa*.
Figure 10D:
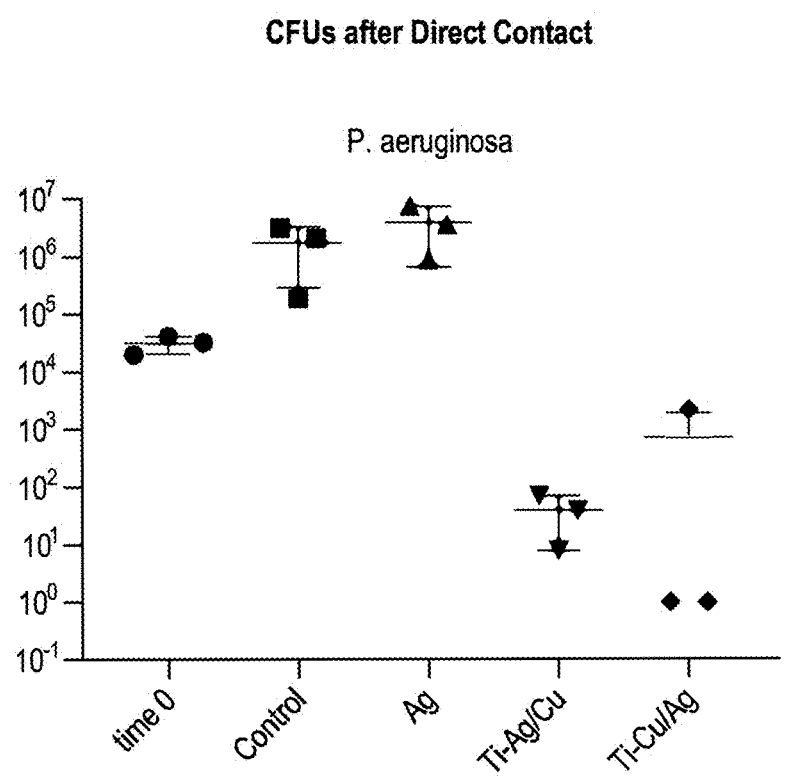
FIG. 10D show results from an ISO 22196-based kill assay for *P. aeruginosa*.

Both sputter coatings produced a very strong resistance to growth compared to the other groups and resulted in either complete kill or several orders of magnitude less CFUs as compared to the time zero (the quantity seeded on each specimen). Bacteria growth was not inhibited by the control or Ag-doped plugs. Superior performance is noted in the near complete kill of methicillin-susceptible *S. aureus* (UAMS-1) (see FIGS. 10A and 10B) and *P. aeruginosa* (ATCC #27317) (FIGS. 10C and 10D). The Live (green)/Dead (red) staining was also consistent with CFU counts, showing little to no live bacteria on the surfaces of sputter coated plugs and bacteria lawn formations on control and Ag-doped plugs after overnight culture.

Log reduction testing is being done on *P. aeruginosa* (ATCC #27317), *S. aureus* (MRSA) (ATCC #33591), *S. epidermidis* (ATCC #12228), *E. faecalis* (ATCC #4082); *S. pyogenes* (ATCC #19615), *P. aeruginosa* (ATCC #27317); *P. acnes* (ATCC #6919), and methicillin-susceptible *S. aureus*.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible. The embodiments described herein are restated and expanded upon in the following paragraphs without explicit reference to the figures.

In many embodiments, a sensor control device includes an electronics housing comprising an upper shell matable to a lower mount having a skin-facing surface; and a plug assembly coupled to the electronics housing and including a sensor module that has a sensor and a sharp module comprising a sharp, the plug assembly comprising a base having a skin-facing surface and a plug portion comprising a lumen therethrough, wherein at least a portion of a surface of the electronics housing or the plug assembly comprises an antimicrobial agent.

In some embodiments, at least one of the upper shell, the skin-facing surface of the lower mount, the skin-facing surface of the base, and the plug portion comprises the antimicrobial agent. In some embodiments, the upper shell of the electronics housing further comprises an outer perimeter lip, and wherein the outer perimeter lip comprises the antimicrobial agent. In some embodiments, the plug portion further comprises an outward facing surface of the plug portion, an upward facing surface of the plug portion, and an exterior surface of the plug portion, and an interior surface of the plug portion, and wherein at least one of the outward facing surface of the plug portion, an upward facing surface of the plug portion, and an exterior surface of the plug portion, and an interior surface of the plug portion comprises the antimicrobial agent. In some embodiments, the plug portion has a shape selected from the group consisting of frustoconical, round, and oval.

In some embodiments, the antimicrobial agent is a metal or a metal oxide.

In some embodiments, the antimicrobial agent is selected from the group consisting of silver, copper, zinc, and combinations thereof.

In some embodiments, the antimicrobial agent is contained in a coating. In some embodiments, the antimicrobial agent is selected from the group consisting of silver, copper, zinc, and combinations thereof. In some embodiments, the antimicrobial agent comprises silver on copper or copper on silver.

In some embodiments, the antimicrobial agent is blended into a bulk material used to make the electronics housing or the plug assembly.

In some embodiments, the antimicrobial agent is incorporated throughout a material used to make the electronics housing or the plug assembly.

In some embodiments, the antimicrobial agent is impregnated into the at least the portion of the surface of the electronics housing or the plug assembly.

In some embodiments, the antimicrobial agent is applied onto the electronics housing or the plug assembly via overmolding.

In some embodiments, the antimicrobial agent is applied onto the electronics housing or the plug assembly via sputter coating to form a layer containing an antimicrobial agent. In some embodiments, a layer of titanium is applied onto the electronics housing before the layer containing the antimicrobial agent is applied. In some embodiments, the antimicrobial agent is a metal or metal oxide. In some embodiments, the layer containing the antimicrobial agent is a layer comprising at least about 5% metal oxide by weight. In some embodiments, the layer containing the antimicrobial agent is a layer comprising between about 2% and about 30% metal oxide by weight. In some embodiments, the layer containing the antimicrobial agent has a thickness between about 500 Å and 10 µm. In some embodiments, the antimicrobial agent is contained in at least one layer that is applied onto the electronics housing or the plug assembly. In some embodiments, the antimicrobial agent is contained in at least two layers that are applied onto the electronics housing or the plug assembly.

In many embodiments, a method includes the steps of: applying a layer containing an antimicrobial agent onto a surface of a sensor control device, the sensor control device comprising: an electronics housing comprising an upper shell having an outer perimeter lip, the upper shell matable to a lower mount having a skin-facing surface; and a plug assembly coupled to the electronics housing and including a sensor module that has a sensor and a sharp module comprising a sharp, the plug assembly comprising a base having a skin-facing surface and a plug portion comprising a lumen therethrough, wherein the surface of the sensor control device is at least one of the upper shell, the outer perimeter lip, the skin-facing surface of the lower mount, the skin-facing surface of the base, and the plug portion.

In some embodiments, the antimicrobial agent is a metal.

In some embodiments, the antimicrobial agent is a metal oxide.

In some embodiments, the antimicrobial agent is selected from the group consisting of silver, copper, zinc, and combinations thereof.

In some embodiments, the antimicrobial agent is silver on copper or copper on silver.

In some embodiments, the method further includes the step of applying a layer of titanium to the surface of the sensor control device before applying the layer containing the antimicrobial agent onto the surface of the sensor control device.

In some embodiments, the layer containing the antimicrobial agent is applied by sputtering. In some embodiments, the antimicrobial agent is applied in an atmosphere comprising an inert gas and an oxidant. In some embodiments, the atmosphere contains between about 5% and about 100% oxidant by partial pressure. In some embodiments, the oxidant is oxygen. In some embodiments, the antimicrobial agent comprises silver, copper, zinc, or combinations thereof. In some embodiments, the inert gas is Argon. In some embodiments, a metal oxide is formed on the surface of the sensor control device.

In some embodiments, the antimicrobial agent is a metal oxide, and the layer containing the antimicrobial agent contains at least about 85% metal oxide.

In some embodiments, the antimicrobial agent is a metal oxide, and the layer containing the antimicrobial agent is a layer comprising between about 2% and about 98% metal oxide by weight.

In some embodiments, applying the layer containing the antimicrobial agent onto the plug portion includes applying the layer onto at least one of an outward facing surface of the plug portion, an upward facing surface of the plug portion, an exterior surface of the plug portion, and an interior surface of the plug portion.

In some embodiments, the plug portion has a shape selected from the group consisting of frustoconical, round, and oval.

In many embodiments, a method includes the step of sputtering a layer containing a metal onto a surface of a sensor control device, the sensor control device comprising: an electronics housing comprising an upper shell having an outer perimeter lip, the upper shell matable to a lower mount having a skin-facing surface; and a plug assembly coupled to the electronics housing and including a sensor module that has a sensor and a sharp module comprising a sharp, the plug assembly comprising a base having a skin-facing surface and a plug portion comprising a lumen therethrough, wherein the surface of the sensor control device is at least one of the upper shell, the outer perimeter lip, the skin-facing surface of the lower mount, the skin-facing surface of the base, and the plug portion.

In some embodiments, the metal comprises silver, copper, zinc, or combinations thereof.

In some embodiments, the metal is sputtered onto the surface of the sensor control device in an atmosphere comprising an inert gas and an oxidant. In some embodiments, the inert gas is Argon. In some embodiments, the oxidant is oxygen. In some embodiments, the atmosphere comprises between about 5% and about 100% oxidant by partial pressure. In some embodiments, the atmosphere comprises at least about 10% oxidant by partial pressure. In some embodiments, a metal oxide is formed on the surface of the sensor control device.

In some embodiments, the method further includes the step of sputtering a layer of titanium to the surface of the sensor control device before applying the layer containing the metal onto the surface of the sensor control device. In some embodiments, sputtering the layer onto the plug portion includes sputtering the layer onto at least one of an outward facing surface of the plug portion, an upward facing surface of the plug portion, an exterior surface of the plug portion, and an interior surface of the plug portion.

In some embodiments, the plug portion has a shape selected from the group consisting of frustoconical, round, and oval.

In many embodiments, a medical device includes: a housing having a skin-facing surface; and a layer containing a metal oxide adjacent the skin-facing surface, wherein the layer is configured to be in contact with a patient's skin, the layer comprising at least about 5% metal oxide by weight.

In some embodiments, the layer comprises between about 2% and about 98% metal oxide by weight.

In some embodiments, the medical device is configured to be in contact with the patient's skin for at least 10 days.

In some embodiments, the medical device is configured to be in contact with the patient's skin for about 10 to about 14 days.

In some embodiments, the layer is sputter coated onto the skin-facing surface.

In some embodiments, the layer is overmolded onto the skin-facing surface.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed:

1. A sensor control device, comprising:
   a glucose sensor comprising a proximal portion configured to be positioned above a user's skin and to be electrically coupled with electronics and a distal portion configured to be transcutaneously positioned through the user's skin and in contact with a bodily fluid of the user, wherein the distal portion is configured to detect an analyte in the bodily fluid;
   an electronics housing comprising an upper shell mateable to a lower mount having a skin-facing surface, wherein the electronics is disposed within the electronics housing; and
   a plug assembly coupled to the electronics housing and including a sensor module that has the glucose sensor and a sharp module comprising a sharp, the plug assembly comprising a base having a skin-facing surface and a plug portion comprising a lumen therethrough,
   wherein at least a portion of the skin-facing surface of the lower mount of the electronics housing or the skin-facing surface of the base of the plug assembly comprises a layer comprising titanium and a layer comprising an antimicrobial agent on the layer comprising titanium.

2. The device of claim 1, wherein the upper shell of the electronics housing further comprises an outer perimeter lip, and wherein the outer perimeter lip further comprises the antimicrobial agent.

3. The device of claim 1, wherein the plug portion further comprises an outward facing surface of the plug portion, an upward facing surface of the plug portion, and an exterior surface of the plug portion, an interior surface of the plug portion, and wherein at least one of the outward facing surface of the plug portion, the upward facing surface of the plug portion, the exterior surface of the plug portion, and the interior surface of the plug portion further comprises the antimicrobial agent.

4. The device of claim 1, wherein the plug portion has a shape selected from a group consisting of frustoconical, round, and oval.

5. The device of claim 1, wherein the antimicrobial agent is a metal or a metal oxide.

6. The device of claim 1, wherein the antimicrobial agent is selected from the group consisting of silver, copper, zinc, and combinations thereof.

7. The device of claim 1, wherein the antimicrobial agent is contained in a coating.

8. The device of claim 7, wherein the antimicrobial agent is selected from a group consisting of silver, copper, zinc, and combinations thereof.

9. The device of claim 1, wherein the antimicrobial agent comprises silver on copper or copper on silver.

10. The device of claim 1, wherein the antimicrobial agent comprises silver and copper.

11. The device of claim 1, wherein the antimicrobial agent is applied onto the electronics housing or the plug assembly via sputter coating to form the layer comprising the antimicrobial agent.

12. The device of claim 11, wherein the antimicrobial agent is a metal or metal oxide.

13. The device of claim 11, wherein the layer comprising the antimicrobial agent comprises at least 5% metal oxide by weight.

14. The device of claim 11, wherein the layer comprising the antimicrobial agent comprises between 2% and 30% metal oxide by weight.

15. The device of claim 11, wherein the layer comprising the antimicrobial agent has a thickness between 500 Å and 10 μm.

* * * * *